(12) United States Patent
Dria et al.

(10) Patent No.: US 11,642,255 B2
(45) Date of Patent: May 9, 2023

(54) BOND PATTERN

(71) Applicant: The Procter & Gamble Company, Cincinnati, OH (US)

(72) Inventors: Ray Dennis Dria, Mason, OH (US); Michael Joseph Page, Cincinnati, OH (US); Joseph Leslie Grolmes, Madeira, OH (US); Scott Alan King, Liberty Township, OH (US); Matthew Steven Ritter, Liberty Township, OH (US); Christopher Colin Arp, Mason, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 1086 days.

(21) Appl. No.: 16/357,685

(22) Filed: Mar. 19, 2019

(65) Prior Publication Data

US 2019/0290504 A1    Sep. 26, 2019

Related U.S. Application Data

(60) Provisional application No. 62/780,520, filed on Dec. 17, 2018, provisional application No. 62/645,483, filed on Mar. 20, 2018.

(51) Int. Cl.
*A61F 13/515* (2006.01)
*A61F 13/511* (2006.01)
(Continued)

(52) U.S. Cl.
CPC ...... *A61F 13/515* (2013.01); *A61F 13/15699* (2013.01); *A61F 13/15756* (2013.01);
(Continued)

(58) Field of Classification Search
CPC .......... A61F 13/15699; A61F 13/15756; A61F 13/511; A61F 13/514; A61F 13/515;
(Continued)

(56) References Cited

U.S. PATENT DOCUMENTS 3,848,594 A    11/1974  Buell
4,610,678 A    9/1986   Weisman et al.
(Continued)

FOREIGN PATENT DOCUMENTS

CN    103179935 A    6/2013
EP    1157681 A2 *  11/2001    ........... A61F 13/496
(Continued)

OTHER PUBLICATIONS

International Search Report, PCT/US2019/022896, dated Jun. 4, 2019, 12 pages.

*Primary Examiner* — Michele M Kidwell
(74) *Attorney, Agent, or Firm* — Sarah M. DeCristofaro; Wednesday G. Shipp

(57) ABSTRACT

A composite includes a first substrate and a second substrate joined in a bonding region, wherein the first substrate comprises a first Peak Force Tensile Strength and the second Peak Force Tensile Strength. The first Peak Force Tensile Strength is greater than or equal to the second Peak Force Tensile Strength. The bonding region has a Bond Density of about 10% to about 22%; and a Composite Tensile Strength at Peak Force that is within about 15% of the second Peak Force Tensile Strength.

10 Claims, 9 Drawing Sheets

(51) Int. Cl.
   *A61F 13/514* (2006.01)
   *A61F 13/15* (2006.01)
   *A61F 13/51* (2006.01)
   *A61F 13/551* (2006.01)
   *A61F 13/53* (2006.01)

(52) U.S. Cl.
   CPC .......... *A61F 13/511* (2013.01); *A61F 13/514* (2013.01); *A61F 13/53* (2013.01); *A61F 13/55115* (2013.01); *A61F 2013/1591* (2013.01); *A61F 2013/51078* (2013.01)

(58) Field of Classification Search
   CPC ................ A61F 13/53; A61F 13/55115; A61F 2013/1591; A61F 2013/51078
   See application file for complete search history.

(56) References Cited

U.S. PATENT DOCUMENTS

| | | | |
|---|---|---|---|
| 4,662,875 A | 5/1987 | Hirotsu et al. | |
| 4,673,402 A | 6/1987 | Weisman et al. | |
| 4,834,735 A | 5/1989 | Alemany et al. | |
| 4,846,815 A | 7/1989 | Scripps | |
| 4,854,984 A | 8/1989 | Ball et al. | |
| 4,888,231 A | 12/1989 | Angstadt | |
| 4,892,536 A | 1/1990 | Desmarais et al. | |
| 4,894,060 A | 1/1990 | Nestegard | |
| 4,919,738 A | 4/1990 | Ball et al. | |
| 3,860,003 B2 | 6/1990 | Buell | |
| 4,946,527 A | 8/1990 | Battrell | |
| 4,990,147 A | 2/1991 | Freeland | |
| 5,037,416 A | 8/1991 | Allen et al. | |
| 5,137,537 A | 8/1992 | Herron et al. | |
| 5,147,345 A | 9/1992 | Young et al. | |
| 5,151,092 A | 9/1992 | Buell et al. | |
| 5,156,793 A | 10/1992 | Buell et al. | |
| 5,167,897 A | 12/1992 | Weber et al. | |
| 5,221,274 A | 6/1993 | Buell et al. | |
| 5,260,345 A | 11/1993 | Desmarais et al. | |
| 5,269,775 A | 12/1993 | Freeland et al. | |
| 5,342,338 A | 8/1994 | Roe | |
| 5,387,207 A | 2/1995 | Dyer et al. | |
| 5,397,316 A | 3/1995 | Lavon et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,607,760 A | 3/1997 | Roe | |
| 5,609,587 A | 3/1997 | Roe | |
| 5,635,191 A | 6/1997 | Roe et al. | |
| 5,643,588 A | 7/1997 | Roe et al. | |
| 5,865,823 A | 2/1999 | Curro | |
| 5,964,742 A * | 10/1999 | McCormack | D04H 1/54 604/380 |
| 5,993,432 A | 11/1999 | Lodge et al. | |
| 6,004,306 A | 12/1999 | Robles et al. | |
| 6,107,537 A | 8/2000 | Elder et al. | |
| 6,120,487 A | 9/2000 | Ashton | |
| 6,410,129 B2 | 6/2002 | Zhang et al. | |
| 6,432,098 B1 | 8/2002 | Kline et al. | |
| 6,673,418 B1 * | 1/2004 | DeOlivera | A61F 13/511 604/370 |
| 6,677,258 B2 | 1/2004 | Carroll et al. | |
| 6,713,159 B1 | 3/2004 | Blenke et al. | |
| 6,717,028 B1 | 4/2004 | Oberstadt | |
| 6,843,134 B2 | 1/2005 | Anderson et al. | |
| 7,056,404 B2 | 6/2006 | McFall et al. | |
| 7,062,983 B2 | 6/2006 | Anderson et al. | |
| 7,250,549 B2 * | 7/2007 | Richlen | A61F 13/496 604/373 |
| 7,435,243 B2 | 10/2008 | Miyamoto | |
| 7,806,883 B2 | 10/2010 | Fossum et al. | |
| 7,819,853 B2 | 10/2010 | Desai et al. | |
| 8,062,279 B2 | 11/2011 | Miyamoto | |
| 8,618,350 B2 | 12/2013 | Mansfield | |
| 8,795,809 B2 | 8/2014 | Mansfield | |
| 8,939,957 B2 | 1/2015 | Raycheck et al. | |
| 9,358,161 B2 | 6/2016 | Lawson et al. | |
| 2002/0034912 A1 * | 3/2002 | Curro | B29C 66/83413 428/103 |
| 2006/0089616 A1 | 4/2006 | Belau et al. | |
| 2007/0293111 A1 * | 12/2007 | Mansfield | A61F 13/15699 604/378 |
| 2009/0258210 A1 | 10/2009 | Iyad et al. | |
| 2012/0316526 A1 | 12/2012 | Rosati et al. | |
| 2013/0082418 A1 | 4/2013 | Curro et al. | |
| 2014/0303583 A1 | 10/2014 | Berrizbeitia | |
| 2015/0126955 A1 | 5/2015 | Sauer et al. | |
| 2015/0173961 A1 | 6/2015 | Powell et al. | |
| 2016/0067116 A1 | 3/2016 | Beckman et al. | |
| 2016/0270972 A1 | 9/2016 | Surushe et al. | |
| 2017/0027768 A1 * | 2/2017 | Stabelfeldt | A61F 13/491 |
| 2017/0056256 A1 | 3/2017 | Smith et al. | |
| 2018/0042777 A1 | 2/2018 | Dalal et al. | |
| 2019/0070042 A1 * | 3/2019 | LaVon | D04H 3/12 |

FOREIGN PATENT DOCUMENTS

| | | |
|---|---|---|
| JP | 3069885 U | 7/2000 |
| JP | 5282020 B2 | 5/2013 |
| JP | 2014090724 A | 5/2014 |
| JP | 2017063942 A | 4/2017 |
| WO | WO9516746 A1 | 6/1995 |
| WO | WO0217842 A2 | 3/2002 |
| WO | WO2014168810 A1 | 10/2014 |

* cited by examiner

BOND PATTERN

FIELD OF THE INVENTION

The present invention relates to mechanically bonded composites, more specifically mechanically bonded composites that are useful in absorbent articles.

BACKGROUND OF THE INVENTION

It has long been known that absorbent articles such as conventional absorbent articles (e.g., diapers, adult incontinence articles, feminine hygiene pads) offer the benefit of receiving and containing urine and/or other bodily exudates (e.g., feces, menses, mixture of feces and urine, mixture of menses and urine, etc.). The assembly of such articles requires joining different components together through various bonding techniques. In doing so, manufacturers must balance bond strength with feel, material costs and processing considerations.

One form of bonding is mechanical bonding, which may be done by high pressure dynamic bonding where the substrates are compressed between an anvil member and the patterned member, as is disclosed in more detail for example in U.S. Pat. Nos. 4,919,738 and 4,854,984. While such bonds may be strong, the laminate that is created can incur significant stress concentration during product application, which can lead to fracture at the bonded locations. In particular, known bond patterns are not designed to sustain high stress from multiple directions. Likewise, known bond patterns include bond shapes, sizes and spacing that enhance tear propagation rather than inhibiting further tearing.

Often glue is added between substrates to improve the mechanical performance of these mechanical, high pressure bonds. However, there is a limited amount of glue that can be added to a bond region, given the dimensions of the article, the overlap area of the bonded substrates, and other physical constraints. Further, it is desirable to use less adhesive due to potential negative odor and costs associated with adhesive. It is also desirable to provide softer and thinner articles, which puts even greater demands on bonds (e.g., smoother feel, less interference with the feel of bonded materials, and inconspicuous or aesthetic designs).

Therefore, there is a need to provide a bonding design that provides for better product performance, such as less tearing. There is a further need to provide bond impressions that are softer and/or gentler on skin. There is also a need to provide bonding zones that are aesthetically pleasing and visually signal that the products will perform as desired. In addition, there is a need to provide said benefits in cost effective manner.

SUMMARY OF THE INVENTION

In one aspect of the present invention, a composite includes a first substrate and a second substrate joined in a bonding region, wherein the first substrate comprises a first Average Peak Force Tensile Strength and the second Average Peak Force Tensile Strength. The first Average Peak Force Tensile Strength is greater than or equal to the second Average Peak Force Tensile Strength. The bonding region may have a Bond Density of about 22% or less. In nonlimiting examples, the bonding region may have a Bond Density of from about 10% to about 22%. In certain embodiments, the bonding region has Average Composite Tensile Strength that is within about 15% of the second Average Peak Force Tensile Strength. Additionally or alternatively, the bonding region may have Average Lateral Peak Peel Strength of at least about 1.75 N/cm and/or an Average Longitudinal Peel Strength of about 4.0 N or greater. The composite may form a portion of an absorbent article.

DETAILED DESCRIPTION OF THE INVENTION

Figure 1:
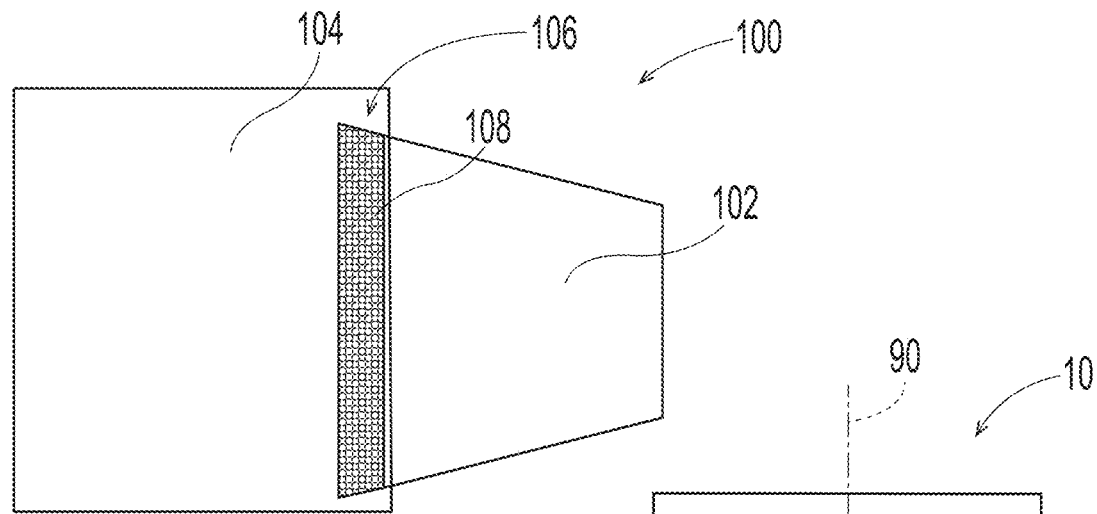
FIG. 1 is a schematic, plan view of an exemplary composite in accordance with a nonlimiting embodiment of the present invention.

"Absorbent article" means a device that absorbs and contains body exudates and, more specifically, devices that are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Disposable," in reference to articles, means that the articles are generally not intended to be laundered or otherwise restored or reused in the same capacity (i.e., they are intended to be discarded after a single use and, preferably, to be recycled, composted or otherwise discarded in an environmentally compatible manner).

"Elastic" and "elastomeric" mean the ability of a material to stretch by at least 100% without rupture or breakage at a given load, and upon release of the load the elastic material or component exhibits at least 80% recovery (i.e., has less than 20% set) in one of the directions as per the Hysteresis Test described herein. Stretch, sometimes referred to as strain, percent strain, engineering strain, draw ratio, or elongation, along with recovery and set may each be determined according to the Hysteresis Test described in more detail below. Materials that are not elastic are referred as inelastic.

"Extensible" means the ability to stretch or elongate, without rupture or breakage, by at least 50% as per step 5(a) in the Hysteresis Test herein (replacing the specified 100% strain with 50% strain).

"Joined" means configurations whereby an element is directly secured to another element by affixing the element directly to the other element, and configurations whereby an element is indirectly secured to another element by affixing the element to intermediate member(s) that in turn are affixed to the other element.

"Laminate" means two or more materials that are bonded to one another by any suitable method known in the art (e.g., adhesive bonding, thermal bonding, ultrasonic bonding, or high pressure bonding using non-heated or heated patterned roll).

"Longitudinal" means a direction lengthwise in a component such that the longitudinal direction runs parallel to the maximum linear dimension in the x-y plane of the component. In an absorbent article as described herein, the longitudinal direction runs substantially perpendicular from a waist end edge to an opposing waist end edge when the absorbent article is in a flat out, uncontracted state, or from a waist end edge to the bottom of the crotch in a bifolded article.

"Lateral" refers to a direction generally perpendicular to the longitudinal direction. In the absorbent article described herein, the lateral direction runs substantially parallel from a side edge to an opposing side edge.

"Machine direction" or "MD" is the direction parallel to the direction of travel of the web in a manufacturing process. The "cross machine direction" or "CD" is the direction substantially perpendicular to the MD and in the plane generally defined by the web.

Bonded Substrates

As shown in FIG. 1, a composite 100 may comprise a first substrate 102 and a second substrate 104 joined in a bonding region 106. The first substrate and/or the second substrate may comprise any suitable materials, including but not limited to nonwovens, films, and combinations thereof. The first and/or second substrate may comprise a laminate of materials. The laminates may be extensible or inextensible. Extensible laminates or substrates may be elastic or inelastic.

Figure 2:
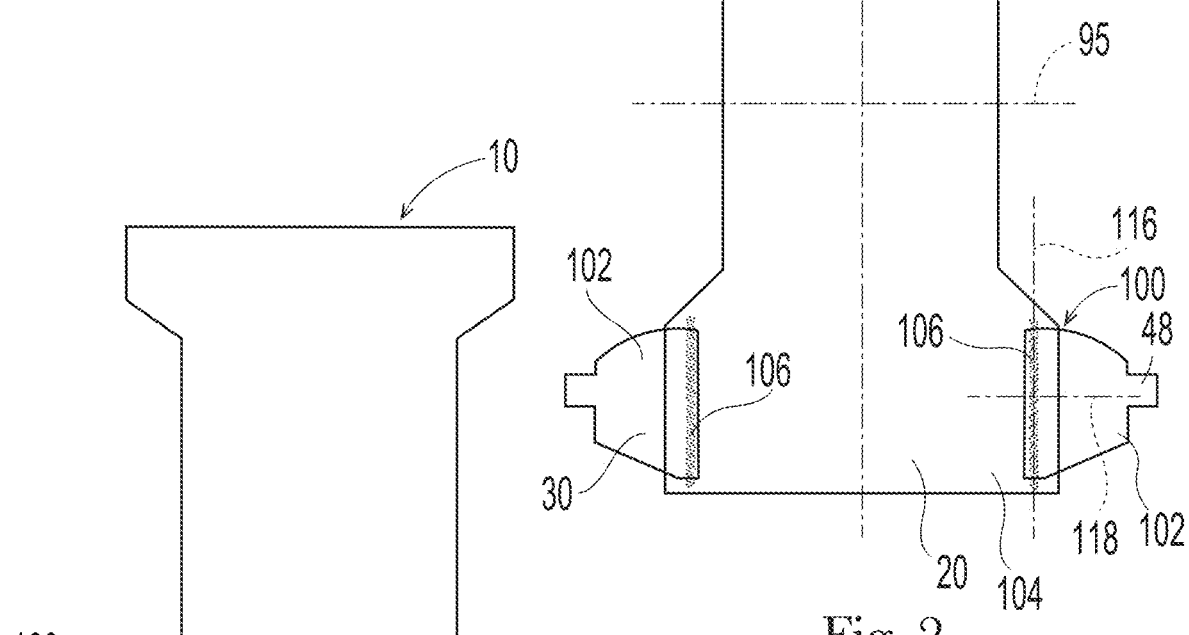
FIG. 2 is a schematic, plan view of an exemplary absorbent article in accordance with a nonlimiting embodiment of the present invention.
Figure 3:
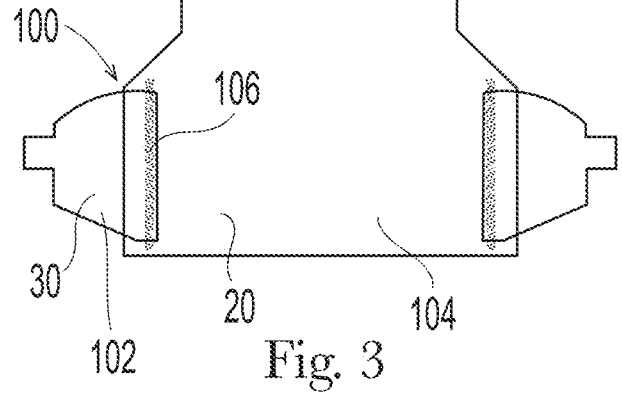
FIG. 3 is a schematic, plan view of another exemplary absorbent article in accordance with a nonlimiting embodiment of the present invention.

The nonlimiting embodiments in FIGS. 2 and 3 are schematic views of exemplary k absorbent articles 10 shown in a flat, uncontracted state. The absorbent articles 10 in the figures comprise the composite 100. In one nonlimiting example, the first substrate 102 comprises a component of the article, such as an ear 30, leg gasketing system 70 or portion thereof, or waist element 80, or other discrete component, each of which may comprise a laminate of materials. The second substrate 104 may comprise a portion of the chassis 20 such as the backsheet, which may be laminated with other components such as the leg cuff material and/or topsheet. In other embodiments, the first substrate 102 may comprise another component of the article, such as the ear 30, and the second substrate may comprise a further component, for example a fastening system 48 and/or fastener 50. Any suitable components of the article may be joined by the bonding described herein. Additional details and features of exemplary absorbent articles are provided below.

The first and second substrates are joined in a bonding region 106. As shown in FIG. 2, the bonding region may comprise a longitudinal axis 116, which in nonlimiting examples is parallel to the longitudinal axis 90 of the article 10. Likewise, the bonding region may comprise a lateral axis 118, which in nonlimiting examples is parallel to the lateral axis 95 of the article 10. Returning to FIG. 1, the bonding region may comprise a plurality of discrete bonds 108. The bonds may be formed by mechanical, including pressure, means. Suitable bonds are formed by dynamic bonding through a pressure biased nip between a patterned element and an anvil member as is disclosed in U.S. Pat. Nos. 4,919,738 and 7,056,404 and U.S. Pat. Pub. No. 2015/0173961. In nonlimiting examples, said bonds are formed under pattern element loading pressure of about 20,000 psi to about 200,000 psi at high line speeds.

The bonds 108 may comprise any suitable shape. In nonlimiting examples, the bonds are circular, elliptical, oval, rings, rods and combinations thereof. The bonds may comprise shapes that are void of, or substantially void of pointed edges (i.e., polygons). Bonds within the plurality may comprise the same shape or different shapes. Likewise, bonds may comprise the same size or different sizes.

In some embodiments, the bonding region may comprise a Bond Density of about 10% or more, or about 12% or more, or about 15% or more, or about 22% or less, or from about 10% to about 22%, or about 15% to about 20% as determined by the Bond Dimensions Test Method herein, reciting for said range every 1% increment therein. In nonlimiting examples, the bonding region may comprise a Minimum Discrete Bond Area Ratio of at least about 14, or at least about 25, or about 105 or less, or from about 20 to about 105, reciting for said range every 5 increment therein, as determined by the Bond Dimensions Test Method herein. In further nonlimiting examples, the bond region may comprise a Maximum Discrete Bond Area Ratio of at least about 8, or at least about 16, or about 25 or less, or about 20 or less, or from about 8 to about 25, or from about 10 to about 20, or from about 15 to about 19, reciting for said ranges every 1 increment therein, as determined by the Bond Dimensions Test Method herein.

In certain embodiments, the bonding region may comprise a Discrete Bond Size Ratio of about 7 or less, about 6.5 or less, or about 2.5 or less, or about 2 or less or from about 1 to about 7, reciting for said range every 0.1 increment therein, as determined by the Bond Dimension Test Method herein. A discrete bond may have a major dimension (the greatest dimension in any direction) of less than 3.5 mm, or 3.4 mm or less. In certain embodiments, the discrete bond comprises a maximum width in the cross direction of 2.2 mm or less, or 2.1 mm or less, or from about 0.5 to about 2.2 mm, reciting for said range every 0.1 mm increment therein. In some embodiments, the bonding region is void of discrete bonds having a major dimension of about 3.5 mm or greater, or about 3 mm or greater or about 2.5 mm or greater, or about 2.2 mm or greater. In certain embodiments, the aspect ratio of the majority of, or all of, the discrete bonds is about 10 or less, or about 5 or less, or about 2.6 or less, or from about 1 to about 10, or from about 1.5 to about 3, reciting for said ranges every 0.1 increment therein.

Additionally, or alternatively, the bonding region may comprise a Minimum Bond Spacing of about 0.8 mm or greater, or about 0.9 mm or greater, or about 1.0 mm or greater, or from about 0.5 to about 1 mm, reciting for said range every 0.1 mm increment therein as determined by the Bond Dimensions Test Method herein. The Minimum Bond Spacing is the minimum distance between the nearest points on two adjacent bonds. In nonlimiting examples, the maximum bond spacing (the maximum distance between nearest points on two adjacent bonds) is small enough that the bonding region comprises a longitudinally interlocking bond pattern and/or a laterally interlocking bond pattern as is discussed below.

The bonding region may comprise an Aggregate Bond Area of 45 $mm^2$ or less, or about 40 $mm^2$ or less, or at least about 25 $mm^2$, or from about 25 $mm^2$ to about 45 $mm^2$, or from about 30 $mm^2$ to about 40 $mm^2$, reciting for said ranges every 0.5 $mm^2$ increment therein, as determined by the Bond Dimensions Test Method herein.

Without being bound by theory, it is believed that said bond sizes, relative sizes, placement and/or bond density result in less tear propagation and greater diffusion of applied stress when the article is in use or being applied. In addition, the specified bond features alone and/or in combination with other principles in this disclosure, are believed to provide a suitable number and placement of bonds to create a self-supporting pattern, such that if one discrete bond ruptures, there are multiple back up bond sites to support the stress applied to the product.

Figure 4A:
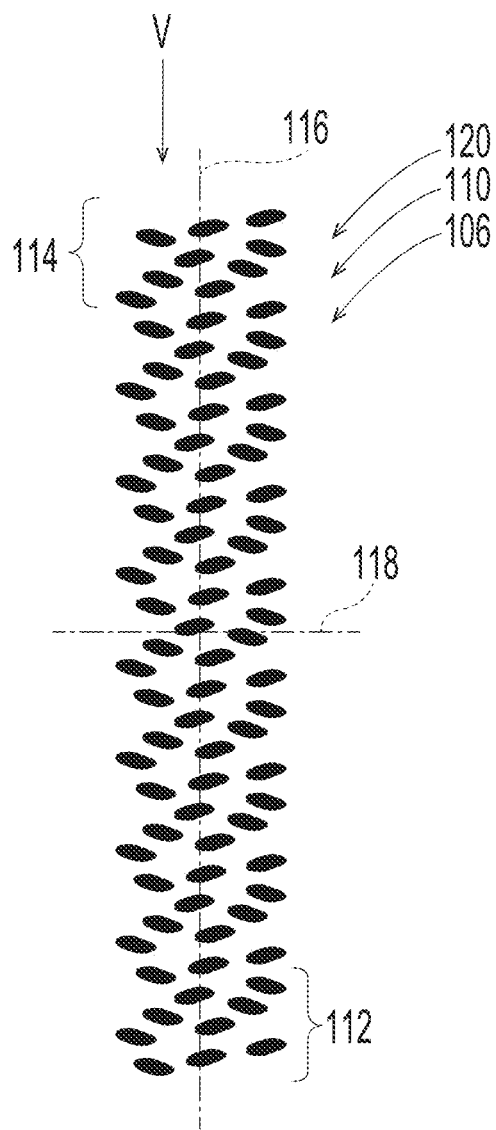
FIGS. 4A-4C are schematic, plan views of an exemplary bond patterns in accordance with nonlimiting embodiments of the present invention.
Figure 4B:
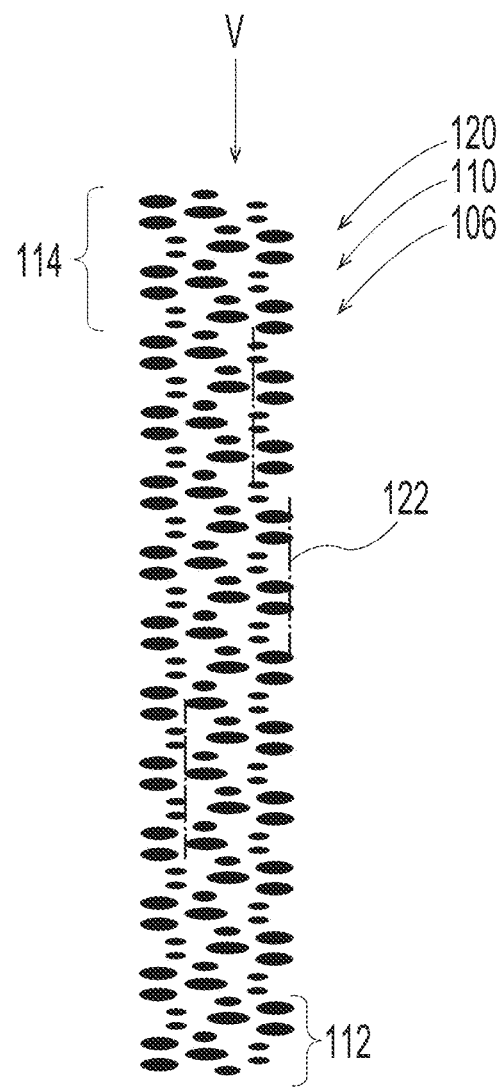

The bonds may be disposed in a pattern 110. The pattern may comprise any of the features noted herein with respect to the bonds. Exemplary patterns 110 are shown in FIGS. 4A and 4B for example. The pattern 110 may comprise a repeat unit 112. The repeat unit may comprise no more than about 15 discrete bonds, or no more than about 12 bonds, or from about 5 bonds to about 15 bonds, reciting for said range every 1 increment therein. In some nonlimiting examples, the repeat unit comprises a longitudinal length of about 15 mm or less, or about 12 mm or less, or about 11 mm or less, or from about 7 mm to about 15 mm, reciting for said range every 0.5 mm increment therein. In further nonlimiting examples, the repeat unit comprises a lateral width about 9 mm or less, or about 8.5 mm or less, or from about 5.5 mm to about 10 mm, reciting for said range every 0.5 mm therein. The repeat unit may comprise discrete bonds of the same size and be void of differently sized bonds. Alternatively, the repeat unit may comprise discrete bonds of different sizes.

Additionally, or alternatively, the bonds 108 may be disposed such that undulations 114 are formed along the periphery of the bonding region on one or more sides. By undulation, it is meant that a portion of the bonds in the bonding region are inset such that the periphery is wavelike or otherwise nonlinear. It is believed that the undulations inhibit long tears because they create a larger path length between adjacent bond sites. Thus, for example with the undulations in FIG. 4A, a tear started at a first bond and extending in the longitudinal direction, can be stopped from propagating further due to the tensile strength of the substrate material prior to reaching the next adjacent bond in longitudinal direction.

In various embodiments, the bonding region may comprise interlocking patterns 120, as shown for example in FIGS. 4A and 4B. The patterns may interlock in the longitudinal direction and/or in the lateral direction. By interlocking, it is meant that a straight line having a thickness of at least 0.2 mm. cannot be drawn throughout the pattern in a given direction without intersecting a portion of a bond. In other words, in a longitudinally interlocking pattern, a line parallel to the longitudinal axis and having a thickness of at least 0.2 mm cannot be drawn through the longitudinal length of the pattern at any point without intersecting a bond or a portion of a bond. Similarly, in a laterally interlocking pattern, a line parallel to the lateral axis and having a thickness of at least 0.2 mm cannot be drawn throughout the width of the pattern at any point without intersecting a bond or a portion of a bond.

In some embodiments, one or more bonds may be disposed at an angle with respect to the longitudinal axis 116 and/or with respect to lateral axis 118 of the bonding region. In nonlimiting examples, each bond in a bonding region may be off-axis as shown in FIG. 4A. By off-axis, it is meant that the major dimension of the bond site is not parallel to the longitudinal or lateral axes. In some nonlimiting examples, bond sites are disposed at an angle of about 20 to about 60 degrees, or about 30 to about 50 degrees, or about 45 degrees with respect to the longitudinal and/or with respect to the lateral axis, reciting for each range every 1 degree increment therein.

Figure 4D:
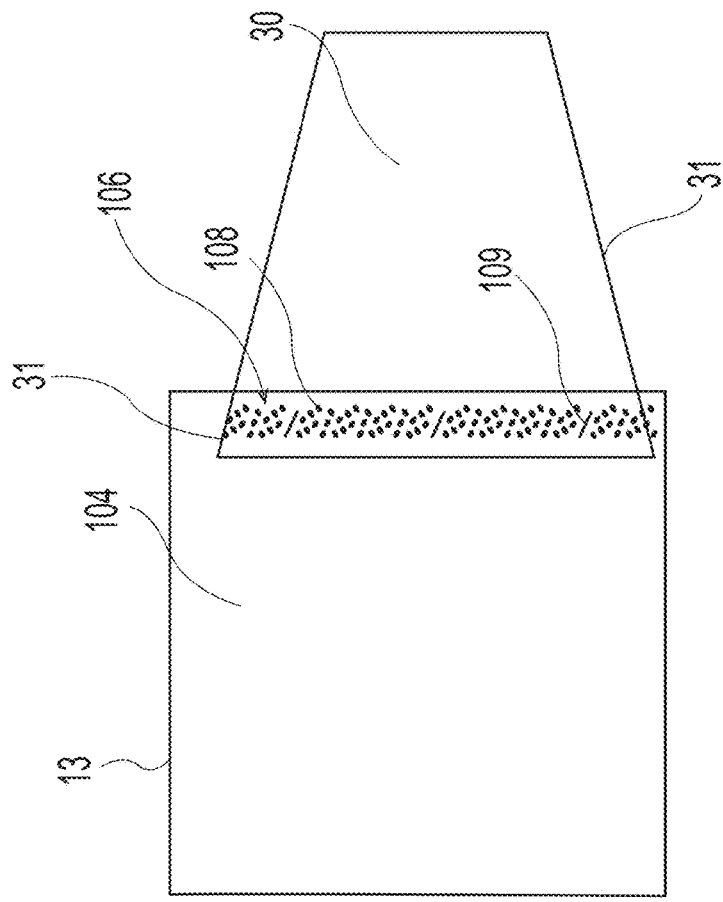
FIG. 4D is a schematic, plan view of an exemplary composite in accordance with a nonlimiting embodiment of the present invention.
Figure 4C:

Turning to FIG. 4C, in certain embodiments, one or more larger discrete bonds 109 are interposed into the pattern. By larger discrete bonds, it is meant that the bonds have a major dimension (i.e., the greatest length in any direction in the x-y plane of the composite) of 3.5 mm or greater. Thus, smaller discrete bonds 107 comprise a major dimension that is less than 3.5 mm. Without being bound by theory, it is believed that introducing a larger discrete bond into a pattern having a majority of smaller discrete bond elements provides secondary benefits to the composite while maintaining strength properties and the ability to withstand multidirectional stress. Secondary benefits may include aesthetic features and reduced contraction from strands of elastic material in the bonding region (as the larger discrete bond elements tend to sever elastic strands during bonding).

The larger discrete bonds 109 can be inserted into the pattern 110 described above in a regular or irregular manner. In nonlimiting examples, no more than 2 larger discrete bonds, or no more than 1 larger discrete bond, may be inserted into one repeat unit 112. In nonlimiting examples, the Ratio of Larger to Smaller Bonds in the pattern may be 2 or less, or 1 or less, or 0.5 or less, as determined by the Bond Dimensions Test Method herein. The introduction of too many larger discrete bonds may undermine the benefits derived from the above-described pattern. The larger discrete bonds may be any suitable shape or size, provided that they comprise a major dimension of at least 3.5 mm. In nonlimiting examples, the larger bonds are in the form of bars, rods or ellipses.

As shown in FIG. 4D, the larger discrete bond can be longitudinally inset from the lateral material edges of the substrates being bonded (such as the lateral edge of a discrete ear 31 and lateral edge of the chassis 13). By insetting the larger bond 109, it is believed that tearing and weakness within the pattern attributable to the larger bond can be avoided. Ruptures in larger bonds can more severely reduce the strength in the bonding region because they propagate to a greater extent than ruptures in smaller bond sites. Thus, it is believed that it is more desirable to locate larger bonds away from areas where forces are applied and tearing is more easily initiated. For example, during application of diapers and use of back ears, forces are typically applied at the lateral material edges of the chassis and ear. By longitudinally insetting the larger bonds, said bonds are placed away from such forces. Thus, the likelihood of detrimental tearing is reduced and the integrity of the bonding region is more likely to remain intact.

Figure 5C:
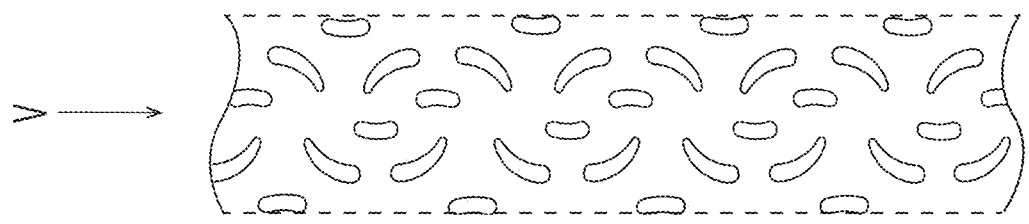
FIG. 5A-5C are schematic, plan views of prior art bond patterns.
Figure 5B:
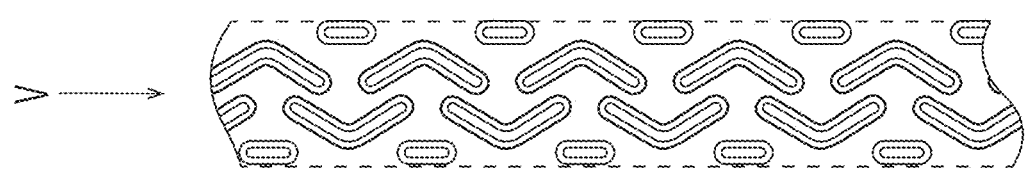
Figure 5A:

Without being bound by theory, it is believed that bonding regions have the features described herein may better withstand stress applied from multiple directions. Indeed, known bonding regions such as the patterns illustrated in FIGS. 5A-5C are not capable of inhibiting tearing or defects formed from stresses applied in certain directions, in particular in the direction shown by the force vector V and vectors within ±75 degrees of the vector. Quite differently, the bonding regions of the present invention can withstand stresses from substantially any direction, including the direction of vector V and vectors at angles within ±75 degrees of V. It is believed the size, placement, shape and other characteristics of the discrete bonds and bond patterns result in better diffusion of stress from multiple directions.

The bonding region may further comprise adhesive bonding 122 as shown for example in FIG. 4B. Adhesive bonding may be continuous or discontinuous. Any suitable form of adhesive known in the art may be used, including but not limited to hot melt adhesives. Additionally or alternatively, the bonding region may comprise other forms of the bonding such as thermobonding, ultrasonic bonding and other bonding known in the art.

Returning to FIG. 1, the composite 100 may comprise Average Composite Tensile Strength that is within about 15% or less, or 12% or less, or about 10% or less, or about 5% or less, or from about 2% to about 18%, or from about 5% to about 15% of the Average Tensile Strength at Peak Force of the weaker of the two substrates/laminates comprising the composite (or either of the substrates if they both comprise substantially the same tensile strength), reciting for each range every 1% increment therein. For instance, the first substrate 102 may comprise a first Average Peak Force Tensile Strength and the second substrate may comprise a second Average Peak Force Tensile Strength, which may be less than the first Average Peak Force Tensile Strength. The Average Peak Force Tensile Strength of the substrates may be determined by the Composite Tensile Strength Test Method herein. The composite may have an Average Composite Tensile Strength that is within 15% or less of the second Average Peak Force Tensile Strength. In this way, the composite substantially retains the strength of the substrate materials.

In certain embodiments, the bonding region of the composite may comprise an Average Longitudinal Peel Strength of at least about 1 N, or at least about 1.15 N as determined by the Longitudinal Peel Strength Test Method herein. In certain embodiments having adhesive bonding, the composite may comprise an Average Longitudinal Peel Strength of at least about 4 N, or at least about 6 N, or at least about 7 N, or from about 5 N to about 10 N, reciting for said range every 1 N increment therein. In embodiments incorporating a small number of larger discrete bonds (i.e., wherein the ratio of larger bonds to smaller bonds is less than 2), the bonding region may comprise an Average Longitudinal Peel Strength of at least about 4 N, or from about 4 N to about 10 N, reciting for said range every 1 N increment therein. In further embodiments, particularly those having no larger discrete bonds, the bonding region may comprise Average Lateral Peel Strength of at least 0.9 N/cm and/or Average Lateral Peak Peel Strength of at least about 1.75 N/cm. In embodiments having adhesive bonding, the composite may comprise Average Lateral Peel Strength of at least about 2.5 N/cm, or at least about 2.6 N/cm and/or Average Lateral Peak Peel Strength of at least about 3.5 N/cm, or at least about 4 N/cm according to the Lateral Peel Strength Test Method herein. In embodiments incorporating a low number of larger bonds (i.e., wherein the ratio of larger bonds to smaller bonds is less than 2), the bonding region may comprise an Average Lateral Peel Strength of at least 0.7 N/cm and/or Average Lateral Peak Peel Strength of at least about 1 N/cm. In embodiments having adhesive bonding and a small number of larger bonds, the composite may comprise Average Lateral Peel Strength of at least about 1.75 N/cm, or at least about 1.8 N/cm and/or Average Lateral Peak Peel Strength of at least about 2.95 N/cm, or at least about 3 N/cm according to the Lateral Peel Strength Test Method herein. The skilled person will recognize that the Longitudinal and Lateral Peel Strengths are dependent on the first and second substrate as well as the bond pattern and material, and sufficiently high peel strength may result in substrate failure. However, the bond patterns and bonding techniques of the present disclosure result in higher peel strength than composites made of the same materials but without the inventive bond patterns and bonding techniques. Further, the inventive patterns better distribute force regardless of the direction in which the force is applied as shown by the examples below.

EXAMPLES

The following composite examples demonstrate properties of the invention herein.

The Comparative Example A comprises an initial set of substrates. The initial exemplary set includes a first substrate that is a ring-rolled activated laminate having an elastic film sandwiched between two nonwovens, where one nonwoven comprises a spunbond web and the other nonwoven comprises a carded web. The laminate layers are joined by adhesive. The laminate is commercially available from Clopay, USA under the trade name ELASTIPRO™ 8004. The laminate is bonded to the second substrate in an inelastic region. The second substrate is a cuff-backsheet laminate comprising a 19 gsm polypropylene spunbond nonwoven material, commercially available from Avgol, USA under tradename AVMN1071984001, a 15 gsm polymeric film, commercially available from Clopay, USA under tradename CLNT0045465363, and a 12 gsm SMS polypropylene nonwoven material commercially available from Berry Global under tradename PGWVN03956. The 19 gsm polypropylene nonwoven is positioned closest to the first substrate, and the 12 gsm SMS nonwoven is positioned furthest away from the first substrate when the composite is formed. The bonding region comprises the pattern shown in FIG. 5A, wherein the repeat length is 30.4 mm in the longitudinal direction. The bonding region comprises a longitudinal axis that is parallel to the longitudinal axis of the second substrate (the cuff-backsheet laminate). The bonds are formed through a pressurized nip between a patterned roll and an anvil roll as disclosed in U.S. Pat. No. 4,919,738. These mechanical bonds extend beyond the maximum longitudinal length of the first substrate in the bonding region.

Comparative Example A (adh) is the same as Comparative Example A except adhesive bonding is also applied in the bonding region. Adhesive is slot coated on the first substrate at an add-on rate of 13 g/m$^2$ with a cross machine width (lateral width in this case) of 12.7 mm and a longitudinal length approximately 10% shorter than the maximum longitudinal length of the first substrate in the bonding region. The adhesive is positioned between the first and second substrate and is approximately centered in both the longitudinal and lateral directions under the mechanical bond pattern. The adhesive is commercially available from Bostik USA under tradename H2401.

Comparative Example B comprises an alternative set of substrates that includes a first substrate that is a ring-rolled activated laminate having an elastic film sandwiched between two nonwovens, where one nonwoven comprises a spunbond web and the other nonwoven comprises a carded web. The laminate layers are joined by adhesive. The laminate is commercially available from Mondi Group, Germany under the trade name PK6508. The laminate is bonded to the second substrate in an inelastic region. The second substrate is a cuff-backsheet laminate comprising a 15 gsm polypropylene spunbond nonwoven material, commercially available from SGN Nonwovens under tradename SGKS184318206, a 15 gsm polymeric film, commercially available from RKW, Germany under tradename RKPA1404198, and a 13 gsm SMS polypropylene nonwoven material commercially available from Pegas Nonwovens under tradename PNELPAG8A19372. The 15 gsm polypropylene nonwoven is positioned closest to the first substrate and the 13 gsm SMS nonwoven is positioned furthest away from the first substrate when the composite is formed. The bonding region comprises the pattern shown in FIG. 5A, wherein the repeat length is 30.4 mm in the longitudinal direction. The bonding region comprises a longitudinal axis that is parallel to the longitudinal axis of the second substrate (the cuff-backsheet laminate). The bonds are formed through a pressurized nip between a patterned roll and an anvil roll as disclosed in U.S. Pat. No. 4,919,738. These mechanical bonds extend beyond the maximum longitudinal length of the first substrate in the bonding region.

Comparative Example B (adh) is the same as Comparative Example B, except adhesive bonding is also applied in the bonding region. Adhesive is slot coated on the first substrate at an add-on rate of 9.3 g/m$^2$ with a cross machine width (lateral width in this case) of 12.7 mm and a longitudinal length approximately 10% shorter than the maximum longitudinal length of the first substrate in the bonding region. The adhesive is positioned between the first and second substrate and is approximately centered in both the longitudinal and lateral directions under the mechanical bond pattern. The adhesive is commercially available from Bostik USA under tradename 4376.

Inventive Example 1 comprises the same first and second substrate as the Comparative Example A (i.e., the initial set). However, the bonding region comprises the pattern shown in FIG. 4A, wherein the repeat length is 10.8 mm in the longitudinal direction. The bonding region comprises a longitudinal axis that is parallel to the longitudinal axis of the second substrate (the cuff-backsheet laminate). The bonds are formed through a pressurized nip between a patterned roll and an anvil roll as disclosed in U.S. Pat. No. 4,919,738. These mechanical bonds extend beyond the maximum longitudinal length of the first substrate in the bonding region.

Inventive Example 1(adh) is the same as Inventive Example 1 except adhesive bonding is also applied. Adhesive is slot coated on the first substrate at an add-on rate of 13 g/m$^2$ with a cross machine width (lateral width in this case) of 12.7 mm and a longitudinal length approximately 10% shorter than the maximum longitudinal length of the first substrate in the bonding region. The adhesive is positioned between the first and second substrate and is approximately centered in both the longitudinal and lateral directions under the mechanical bond pattern. The adhesive is commercially available from Bostik USA under tradename H2401.

Inventive Example 2 comprises the same first and second substrates as the Comparative Example A (i.e., the initial set). However, the bonding region comprises the pattern shown in FIG. 4B, wherein the repeat length is 10 mm in the longitudinal direction. The bonding region comprises a longitudinal axis that is parallel to the longitudinal axis of the second substrate (the cuff-backsheet laminate). The bonds are formed through a pressurized nip between a patterned roll and an anvil roll as disclosed in U.S. Pat. No. 4,919,738. These mechanical bonds extend beyond the maximum longitudinal length of the first substrate in the bonding region.

Inventive Example 2(adh) is the same as Inventive Example 2 except adhesive bonding is also applied. Adhesive is slot coated on the first substrate at an add-on rate of 13 g/m$^2$ with a cross machine width (lateral width in this case) of 12.7 mm and a longitudinal length approximately 10% shorter than the maximum longitudinal length of the first substrate in the bonding region. The adhesive is positioned between the first and second substrate and is approximately centered in both the longitudinal and lateral directions under the mechanical bond pattern. The adhesive is commercially available from Bostik USA under tradename H2401.

Inventive Example 3(adh) comprises the same first and second substrate as the Comparative Example B (i.e., the alternative set). However, the bonding region comprises the pattern shown in FIG. 4A, wherein the repeat length is 10.8 mm in the longitudinal direction. The bonding region comprises a longitudinal axis that is parallel to the longitudinal axis of the second substrate (the cuff-backsheet laminate). The bonds are formed through a pressurized nip between a patterned roll and an anvil roll as disclosed in U.S. Pat. No. 4,919,738. These mechanical bonds extend beyond the maximum longitudinal length of the first substrate in the bonding region. Adhesive bonding is also applied. Adhesive is slot coated on the first substrate at an add-on rate of 9.3 g/m² with a cross machine width (lateral width in this case) of 12.7 mm and a longitudinal length approximately 10% shorter than the maximum longitudinal length of the first substrate in the bonding region. The adhesive is positioned between the first and second substrate and is approximately centered in both the longitudinal and lateral directions under the mechanical bond pattern. The adhesive is commercially available from Bostik USA under tradename 4376.

Inventive Example 4 comprises the same first and second substrates as the Comparative Example B (i.e., the alternative set). However, the bonding region comprises the pattern shown in FIG. 4C. The bonding region comprises a longitudinal axis that is parallel to the longitudinal axis of the second substrate (the cuff-backsheet laminate). The bonds are formed through a pressurized nip between a patterned roll and an anvil roll as disclosed in U.S. Pat. No. 4,919,738. These mechanical bonds extend beyond the maximum longitudinal length of the first substrate in the bonding region.

Inventive Example 4(adh) is the same as Inventive Example 4 except adhesive bonding is also applied. Adhesive is slot coated on the first substrate at an add-on rate of 9.3 g/m² with a cross machine width (lateral width in this case) of 12.7 mm and a longitudinal length approximately 10% shorter than the maximum longitudinal length of the first substrate in the bonding region. The adhesive is positioned between the first and second substrate and is approximately centered in both the longitudinal and lateral directions under the mechanical bond pattern. The adhesive is commercially available from Bostik USA under tradename 4376.

For clarity, Table 1 identifies which examples have the same substrates.

TABLE 1

| Substrates in the Composite | Comparative Example | Inventive Examples |
|---|---|---|
| Initial set | Comparative Examples A and A (adh) | Inventive Examples 1, 1(adh), 2 and 2(adh) |
| Alternative set | Comparative Examples B and B (adh) | Inventive Examples 3(adh), 4 and 4(adh) |

Tables 2 and 3 show dimensions of the bond patterns.

TABLE 2

Bond Density and Relative Area

| Example | Number of Bonds in Repeat Unit | Aggregate Bond Area (mm²) | Bond Density % | Min. Discrete Bond Area Ratio | Maximum Discrete Bond Area Ratio | Discrete Bond Size Ratio | Max Aspect Ratio of Discrete Bond |
|---|---|---|---|---|---|---|---|
| Comparative Examples A and A(adh) | 6 | 47.07 | 23.5% | 13.2 | 6.3 | 2.1 | 14.4 |
| Comparative Examples B and B(adh) | 6 | 47.07 | 23.5% | 13.2 | 6.3 | 2.1 | 14.4 |
| Inventive Examples 1 and 1(adh) | 9 | 32.11 | 15.4% | 25.1 | 18.7 | 1.3 | 2.6 |
| Inventive Examples 2 and 2(adh) | 12 | 39.82 | 19.9% | 103.4 | 16.3 | 6.4 | 1.8 |
| Inventive Example 3(adh) | 9 | 32.11 | 15.4% | 25.1 | 18.7 | 1.3 | 2.6 |
| Inventive Example 4 and 4(adh) | 9 with larger bond interposing in repeat cell | 32.97 | 16.6% | 22.7 | 8.5 | 2.7 | 18 |

TABLE 3

Bond Density and Comparison of Larger and Smaller Discrete Bonds

| Example | Number of Bonds in Repeat Unit | Aggregate Bond Area (mm²) | Bond Density % | Max Aspect Ratio of Discrete Bond | Aggregate Area of Smaller Bonds (mm²) | Aggregate Area of Larger Bonds (mm²) | Ratio of Larger Bonds to Smaller Bonds |
|---|---|---|---|---|---|---|---|
| Comparative Examples A and A (adh) | 6 | 47.07 | 23.5% | 14.4 | 11.94 | 35.13 | 2.9 |
| Comparative Examples B and B(adh) | 6 | 47.07 | 23.5% | 14.4 | 11.94 | 35.13 | 2.9 |
| Inventive Examples 1 and 1(adh) | 9 | 32.11 | 15.4% | 2.6 | 32.11 | 0.00 | 0.0 |
| Inventive Examples 2 and 2(adh) | 12 | 39.82 | 19.9% | 1.8 | 39.82 | 0.00 | 0.0 |
| Inventive Example 3(adh) | 9 | 32.11 | 15.4% | 2.6 | 32.11 | 0.00 | 0.0 |
| Inventive Examples 4 and 4(adh) | 9 with larger bond interposing in repeat cell | 32.97 | 16.6% | 18 | 29.10 | 3.88 | 0.1 |

Table 4 shows the Composite Tensile Strengths of the examples as well as the Peak Force Tensile Strength of the second substrate in the respective composites. The second substrate is the weaker of the two substrates in the composites. As can be seen below, the inventive examples maintained much of the tensile strength properties of the substrate even after bonding. Importantly, the bond pattern in the inventive examples can maintain the tensile strength properties without the assistance of adhesive bonding while the comparative examples are not able to do so. Without being bound by theory, it is believed that the mechanical bonding of the inventive patterns provide more strength to the composites than the comparative bond patterns. Adhesive is believed to provide more necessary strength (composite strength, longitudinal peel strength and lateral peel strength) for the comparative patterns while the inventive patterns are less reliant on adhesive. Stated differently, the inventive patterns contribute more strength and drive better performance than the comparative patterns, as shown in the following tables.

TABLE 4

Composite Tensile Strength

| Example | With or Without Glue Assist | Average Composite Tensile Strength (N/cm) |
| --- | --- | --- |
| Comparison of Composites Having Initial Set of Substrates | | |
| Second Substrate in Initial Set without bond pattern | N/A | 7.76 ± 0.89 N/cm* (*Substrate Average Peak Force Tensile Strength not Composite Tensile Strength) |
| Comparative Example A | No Glue | 5.24 ± 0.07 N/cm |
| Inventive Example 1 | No Glue | 7.17 ± 0.23 N/cm |
| Inventive Example 2 | No Glue | 7.48 ± 0.38 N/cm |
| Comparative Example A(adh) | With Glue | 6.15 ± 0.72 N/cm |
| Inventive Example 1(adh) | With Glue | 7.42 ± 0.61 N/cm |
| Inventive Example 2(adh) | With Glue | 8.16 ± 1.03 N/cm |
| Comparison of Composites Having Alternative Set of Substrates | | |
| Second Substrate in Alternative Set without bond pattern | N/A | 7.37 ± 0.79 N/cm* (*Substrate Average Peak Force Tensile Strength not Composite Tensile Strength) |
| Comparative Example B | No Glue | 4.26 ± 0.56 N/cm |
| Inventive Example 4 | No Glue | 6.39 ± 0.52 N/cm |
| Comparative Example B(adh) | With Glue | 6.26 ± 0.36 N/cm |
| Inventive Example 3(adh) | With Glue | 6.53 ± 0.61 N/cm |
| Inventive Example 4(adh) | With Glue | 6.82 ± 0.80 N/cm |

Table 5 compares the Longitudinal Peel Strength of the various examples. The Average Longitudinal Peel Strength (as determined by the Longitudinal Peel Strength Test herein) of the Inventive Examples is greater than that of the Comparative Examples. Without being bound by theory, it is believed that these inventive bond patterns allow forces to be better distributed during use or application of products incorporating the composite. The Average Longitudinal Peel Strength is a proxy for a back ear-backsheet/cuff laminate composite's ability to withstand stresses experienced during application and use of an absorbent article. Indeed, undesirable tearing often occurs in the longitudinal direction. As noted above, adhesive is believed to provide more necessary strength (composite strength, longitudinal peel strength and lateral peel strength) for the comparative patterns while the inventive patterns are less reliant on adhesive.

TABLE 5

Longitudinal Peel Strength

| Bond Pattern | With or Without Glue Assist | Average Longitudinal Peel Strength (N) |
| --- | --- | --- |
| Comparative Example A | No Glue | 0.89 ± 0.11N |
| Inventive Example 1 | No Glue | 1.17 ± 0.08N |
| Inventive Example 2 | No Glue | 1.11 ± 0.10N |
| Comparative Example A(adh) | With Glue | 4.94 ± 0.84N |
| Inventive Example 1(adh) | With Glue | 7.49 ± 0.66N |
| Inventive Example 2(adh) | With Glue | 9.44 ± 1.63N |
| Comparative Example B | No Glue | 0.64 ± 0.11N |
| Inventive Example 4 | No Glue | 0.99 ± 0.02N |
| Comparative Example B(adh) | With Glue | 3.83 ± 0.26N |
| Inventive Example 3(adh) | With Glue | 4.22 ± 0.13N |
| Inventive Example 4(adh) | With Glue | 3.98 ± 0.37N |

Table 6 compares the Lateral Peel Strength and Lateral Peak Peel Strengths of the various examples. The Average Lateral Peel and Peak Peel Strengths (as determined by the Lateral Peel Strength Test herein) of the Inventive Examples are greater than that of the Comparative Example. Without being bound by theory, it is believed that the inventive bond patterns allow forces to be better distributed when exerted during use or application of products incorporating the composite. Together with Table 5, it can be seen that the inventive patterns better distribute force regardless of the direction in which the force is applied. This is especially important in preventing tears, for example along an edge of a bonded ear or leg cuff. Likewise, it can be seen that the inventive patterns are less reliant on adhesive for peel strength.

TABLE 6

Lateral Peel Strength

| Bond Pattern | With or Without Glue Assist | Average Lateral Peel Strength (N/cm) | Average Lateral Peak Peel Strength (N/cm) |
| --- | --- | --- | --- |
| Comparative Example A | No Glue | 0.79 ± 0.12 N/cm | 1.72 ± 0.28 N/cm |
| Inventive Example 1 | No Glue | 0.95 ± 0.19 N/cm | 1.80 ± 0.34 N/cm |
| Inventive Example 2 | No Glue | 0.90 ± 0.14 N/cm | 1.79 ± 0.23 N/cm |
| Comparative Example A(adh) | With Glue | 2.28 ± 0.10 N/cm | 3.48 ± 0.29 N/cm |
| Inventive Example 1(adh) | With Glue | 2.71 ± 0.07 N/cm | 4.24 ± 0.15 N/cm |
| Inventive Example 2(adh) | With Glue | 2.62 ± 0.11 N/cm | 3.98 ± 0.14 N/cm |
| Comparative Example B | No Glue | 0.57 ± 0.05 N/cm | 0.93 ± 0.04 N/cm |
| Inventive Example 4 | No Glue | 0.70 ± 0.04 N/cm | 1.14 ± 0.06 N/cm |
| Comparative Example B(adh) | With Glue | 1.67 ± 0.08 N/cm | 2.82 ± 0.10 N/cm |
| Inventive Example 3(adh) | With Glue | 1.84 ± 0.05 N/cm | 3.04 ± 0.05 N/cm |
| Inventive Example 4(adh) | With Glue | 1.93 ± 0.06 N/cm | 3.03 ± 0.19 N/cm |

Article Comprising the Composite

Figure 6:
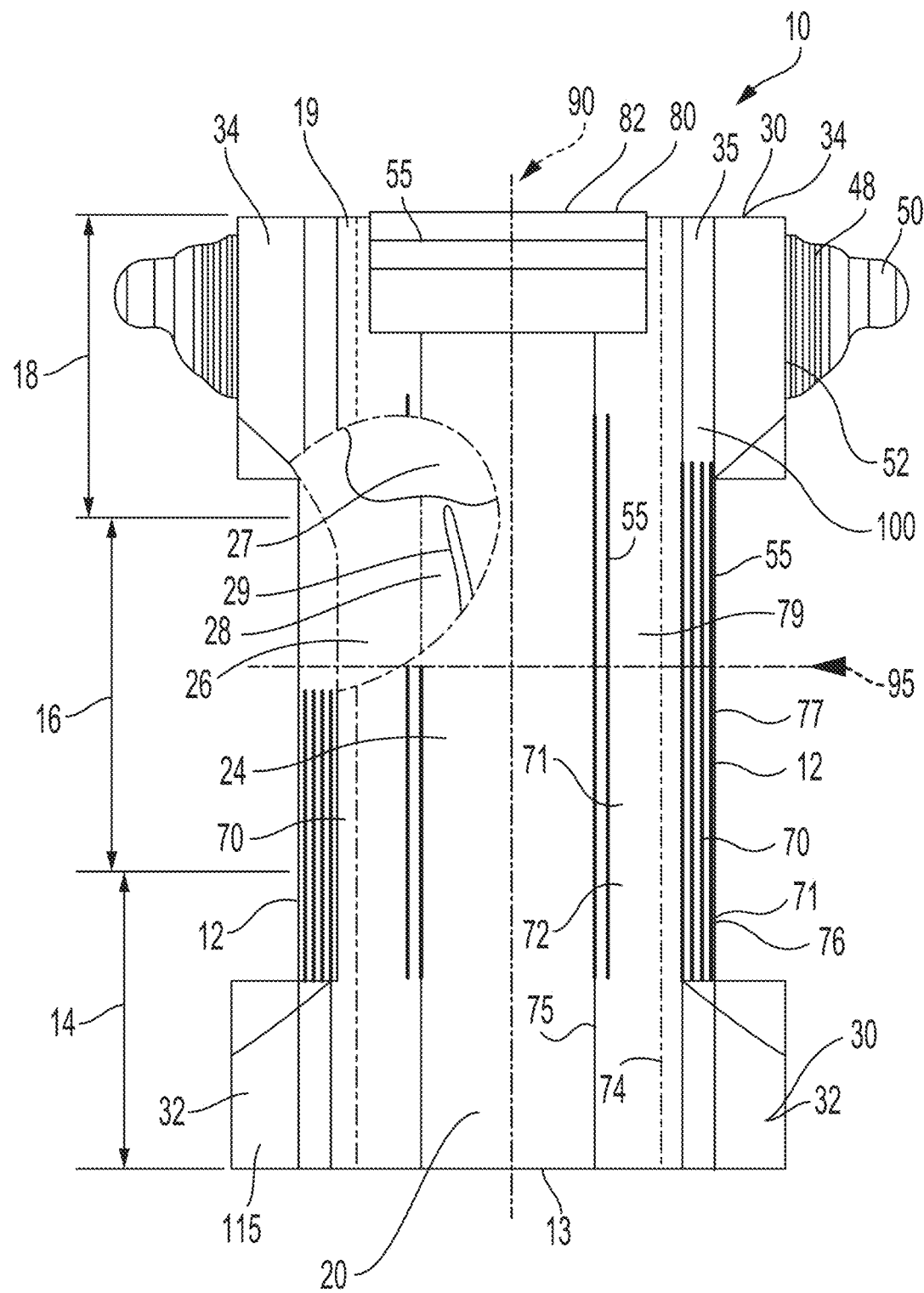
FIG. 6 is schematic, plan view of an exemplary absorbent article according to a nonlimiting embodiment of the present invention. The absorbent article is shown in a flat, uncontracted state.

FIG. 6 is a plan view of an exemplary, nonlimiting embodiment of an absorbent article 10 of the present invention in a flat, uncontracted state. The body-facing surface 115 of the absorbent article 10 is facing the viewer. The absorbent article 10 includes a longitudinal centerline 90 and a lateral centerline 95.

The absorbent article 10 comprises a chassis 20. The absorbent article 10 and chassis 20 are shown to have a first waist region 14, a second waist region 18 opposed to the first waist region 14, and a crotch region 16 located between the first waist region 14 and the second waist region 18. The waist regions 14 and 18 generally comprise those portions of the absorbent article 10 which, when worn, encircle the waist of the wearer. The waist regions 14 and 18 may include elastic members 55 such that they gather about the waist of the wearer to provide improved fit and containment. The crotch region 16 is the portion of the absorbent article 10 which, when the absorbent article 10 is worn, is generally positioned between the legs of the wearer.

The outer periphery of the chassis 20 is defined by longitudinal edges 12 and waist edges (first waist edge 13 in first waist region 14 and second waist edge 19 in second waist region 18). The chassis 20 may have opposing longitudinal edges 12 that are oriented generally parallel to the longitudinal centerline 90. However, for better fit, longitudinal edges 12 may be curved or angled to produce, for example, an "hourglass" shape article when viewed in a plan view as shown in FIG. 1. The chassis 20 may have opposing lateral edges 13, 19 (i.e., the first waist edge 13 and second waist edge 19) that are oriented generally parallel to the lateral centerline 95.

The chassis 20 may comprise a liquid permeable topsheet 24, a backsheet 26, and an absorbent core 28 between the topsheet 24 and the backsheet 26. The absorbent core may comprise absorbent material, including for example superabsorbent particles and absorbent gelling materials (AGM). The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In some embodiments, an acquisition-distribution system 27 is disposed between the topsheet 24 and the absorbent core 28. Articles of the present invention may comprise an Average Number of Particles Per Pad of 20 or less, or 15 or less, or 10 or less as determined by the Topsheet AGM Residue (TAGMR) Method herein. In nonlimiting examples, articles of the present invention may comprise a Percentage of Pads with No Residue Particles of at least 20%, or at least 50%, or from 10% to 100% reciting for said range every 10% increment therein as determined by the TAGMR Method herein. In this way, the absorbent material is kept away from the skin of the wearer.

In certain embodiments, the chassis 20 comprises the main structure of the absorbent article 10 with other features added to form the composite absorbent article structure. While the topsheet 24, the backsheet 26, and the absorbent core 28 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

The composite 100 of the present invention may be formed by one or more components of the article, including but not limited to the chassis, ear, leg cuff, waist elements and combinations thereof.

Topsheet:

The topsheet 24 is generally a portion of the absorbent article 10 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, Tenn. as supplier code 055SLPV09U. The topsheet 24 may be apertured.

Any portion of the topsheet 24 may be coated with a lotion or skin care composition as is known in the art. Non-limiting examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

Absorbent Core:

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials (AGM); or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In some embodiments, the absorbent core may comprise one or more channels 29, wherein said channels are substantially free of absorbent particulate polymer material. The channels 29 may extend longitudinally or laterally. The absorbent core may further comprise two or more channels. The channels may be straight, curvilinear, angled or any workable combination thereof. In nonlimiting examples, two channels are symmetrically disposed about the longitudinal axis. In some embodiments, the core may comprise the composite of the present invention.

Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316, and U.S. patent application Ser. Nos. 13/491,642 and 15/232,901.

Backsheet:

The backsheet 26 is generally positioned such that it may be at least a portion of the garment-facing surface of the absorbent article 10. Backsheet 26 may be designed to prevent the exudates absorbed by and contained within the absorbent article 10 from soiling articles that may contact the absorbent article 10, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 10 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co. of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. The outer cover may be made of a soft, non-woven material. The inner layer may be made of a substantially liquid-impermeable film, such as a polymeric film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

Ears/Fasteners:

The absorbent article 10 may include one or more ears 30, including for example front ears 32 disposed in the first waist region and/or back ears 34 disposed in the second waist region. The ears 30 may be integral with the chassis or discrete elements joined to the chassis 20 at a chassis attachment bond 35, which may join one or more layers of the ear to the chassis. The ears 30 may be extensible or elastic. The ears 30 may be formed from one or more nonwoven webs, woven webs, knitted fabrics, polymeric and elastomeric films, apertured films, sponges, foams, scrims, or combinations and/or laminates of any the foregoing.

In some embodiments, the ear 30 may include elastomers, such that the ear is stretchable. In certain embodiments, the ears 30 may be formed of a stretch laminate such as a nonwoven/elastomeric material laminate or a nonwoven/elastomeric material/nonwoven laminate, which also results in the ear being stretchable. The ear 30 may be extensible in the lateral direction of the article. In some embodiments, the ear is elastic in the lateral direction. In further embodiments, the ear 30 may extend more in the lateral direction than in the longitudinal direction. Alternatively, the ear may extend more in the longitudinal direction than in the lateral direction. In certain nonlimiting examples, the ear may include one or more inelastic regions along with a separate elastic region.

In some embodiments, the ear comprises a laminate of one or more nonwovens and one or more elastic materials. The elastomeric material may be sandwiched between two nonwovens. Additional layers may be included (e.g., additional nonwovens, inelastic materials, elastic or extensible materials, etc.).

Any suitable nonwoven may be used in an ear 30. Suitable nonwovens may comprise a basis weight of at least about 8 gsm, or less than about 22 gsm, or about 17 gsm or less, or from about 10 gsm to about 17 gsm, reciting for said range every 1 increment therein. Where the ear 30 comprises more than one nonwoven, the nonwovens may comprise the same basis weight or different basis weights. Likewise, the nonwovens may comprise the same layer structure or different layer structures. Further, a nonwoven in the ear may comprise the same or different features of nonwovens in the backsheet, topsheet, leg gasketing system and/or waist feature.

Nonlimiting examples of suitable elastomeric materials include film (e.g., polyurethane films, films derived from rubber and/or other polymeric materials), an elastomeric coating applied to another substrate (e.g., a hot melt elastomer, an elastomeric adhesive, printed elastomer or elastomer co-extruded to another substrate), elastomeric non-wovens, scrims, and the like. Elastomeric materials can be formed from elastomeric polymers including polymers comprising styrene derivatives, polyesters, polyurethanes, polyether amides, polyolefins, combinations thereof or any suitable known elastomers including but not limited to co-extruded VISTAMAXX®. Exemplary elastomers and/or elastomeric materials are disclosed in U.S. Pat. Nos. 8,618,350; 6,410,129; 7,819,853; 8,795,809; 7,806,883; 6,677,258 and U.S. Pat. Pub. No. 2009/0258210. Commercially available elastomeric materials include KRATON (styrenic block copolymer; available from the Kraton Chemical Company, Houston, Tex.), SEPTON (styrenic block copolymer; available from Kuraray America, Inc., New York, N.Y.), VECTOR (styrenic block copolymer; available from TSRC Dexco Chemical Company, Houston, Tex.), ESTANE (polyurethane; available from Lubrizol, Inc, Ohio), PEBAX (polyether block amide; available from Arkema Chemicals, Philadelphia, Pa.), HYTREL (polyester; available from DuPont, Wilmington, Del.), VISTAMAXX (homopolyolefins and random copolymers, and blends of random copolymers, available from EXXON Mobile, Spring, Tex.) and VERSIFY (homopolyolefins and random copolymers, and blends of random copolymers, available from Dow Chemical Company, Midland, Mich.).

The ear may be activated by processes disclosed in U.S. Pat. Pub. No. 2013/0082418, U.S. Pat. Nos. 5,167,897; 5,993,432; 5,156,793; 5,167,897; 7,062,983 and 6,843,134 for example. The ear may comprise an ultrasonically bonded ear as is disclosed for example in U.S. patent application Ser. No. 15/674,559.

The ear may be joined to the chassis at a chassis attachment bond 35. The chassis attachment bond may comprise the bonding region 106 of the composite, where the composite comprises the chassis and the ear as first and second substrates. In some nonlimiting examples, the chassis attachment bond is located in an inelastic region of the ear.

The absorbent article 10 may also include a fastening system 48. When fastened, the fastening system 48 interconnects the first waist region 14 and the rear waist region 18 resulting in a waist circumference that may encircle the wearer during wear of the absorbent article 10. The fastening system 48 may comprise a fastening elements 50 such as tape tabs, hook and loop fastening components, interlocking fasteners such as tabs & slots, buckles, buttons, snaps, and/or hermaphroditic fastening components, although any other known fastening means are generally acceptable. The absorbent article may further comprise a landing zone to which a fastening element can engage and/or a release tape that protects the fastening elements from insult prior to use. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. In some embodiments, the fastening system 48 and/or the element 50 is foldable.

The fastening system 48 may be joined to any suitable portion of the article 10 by any suitable means. In some embodiments, the fastening system is joined to the ear 30 at a fastener attachment bond 52 as illustrated in FIG. 6. The fastening system may be joined to the ear between layers. The fastener attachment bond 52 may comprise the bonding region 106 of a composite in accordance with the present disclosure.

Leg Gasketing System:

The absorbent article 10 may comprise a leg gasketing system 70 attached to the chassis 20, which may comprise one or more cuffs 71. The leg gasketing system may comprise a pair of barrier leg cuffs 72. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximal edge joined directly or indirectly to the topsheet 24 and/or the backsheet 26 and a free terminal edge 75, which is intended to contact and form a seal with the wearer's skin. In some embodiments, the free terminal edge 75 comprises a folded edge. The barrier leg cuffs 72 extend at least partially between the front waist edge 13 and the rear waist edge 19 of the absorbent article on opposite sides of the longitudinal centerline 100 and are at least present in the crotch region. The barrier leg cuffs may be joined at the proximal edge with the chassis of the article by a bond which may be made by gluing, fusion bonding, or a combination of other suitable bonding processes.

The barrier leg cuffs may be integral with the topsheet 24 or the backsheet 26 or may be a separate material joined to the article's chassis. Each barrier leg cuff 72 may comprise one, two or more elastic elements 55 close to the free terminal edge 75 to provide a better seal.

In addition to the barrier leg cuffs 72, the article may comprise gasketing cuffs 76, which are joined to the chassis of the absorbent article, in particular to the topsheet 24 and/or the backsheet 26 and are placed externally relative to the barrier leg cuffs 72. The gasketing cuffs 76 may provide a better seal around the thighs of the wearer. A gasketing cuff may comprise a proximal edge and a free terminal edge 77. The free terminal edge 77 may comprise a folded edge. Each gasketing cuff may comprise one or more elastic elements 55 in the chassis of the absorbent article between the topsheet 24 and backsheet 26 in the area of the leg openings. All, or a portion of, the barrier leg cuffs and/or gasketing cuffs may be treated with a lotion or another skin care composition.

In further embodiments, the leg gasketing system comprises barrier leg cuffs that are integral with gasketing cuffs. Suitable leg gasketing systems which may be part of the absorbent article are disclosed in U.S. Pat. App. No. 62/134, 622, Ser. No. 14/077,708; U.S. Pat. Nos. 8,939,957; 3,860, 003; 7,435,243; 8,062,279.

The leg gasketing system may be attached to the chassis at a cuff attachment bond 79, which may comprise the bonding region of a composite in accordance with the present disclosure.

Elastic Waist Feature:

The absorbent article 10 may comprise at least one elastic waist feature 80 that helps to provide improved fit and containment, as shown in FIG. 6. The elastic waist feature 80 is generally intended to expand and contract to dynamically fit the wearer's waist. Elasticized waist features include waistbands, waist cuffs having pockets formed from a portion of the waist feature 80 that is unattached from the chassis 20, and waist panels designed to fit securely about the abdomen of the wearer. Nonlimiting examples of elasticized waist features are disclosed in U.S. patent application Ser. Nos. 13/490,543; 14/533,472; and 62/134,622. Waist features 80 may be joined to the chassis 20 in the first waist region 14 and/or in the second waist region 18. The waist feature can be used in conjunction with the ear 30 to provide desirable stretch and flexibility for proper fit of the article on the wearer. The waist feature may be attached to the chassis at a waist feature bond 82, which may comprise a bonding region of a composite in accordance with the present disclosure.

Package

The absorbent articles 10 of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 16:
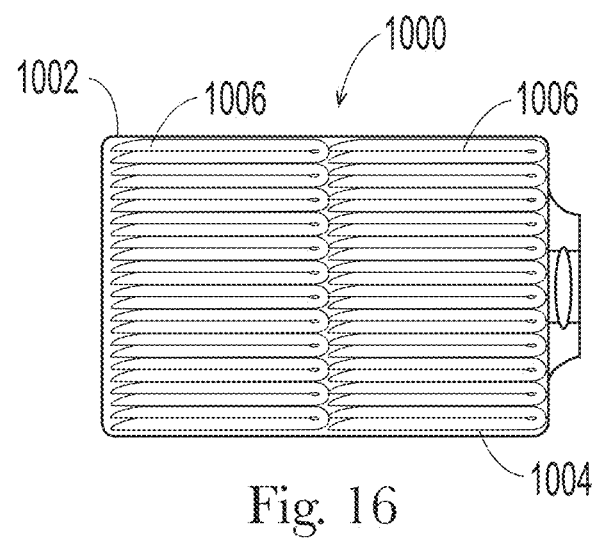
FIG. 16 is a schematic, perspective view of a package in accordance with a nonlimiting embodiment of the present invention.

FIG. 16 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Test Methods

Bond Dimension Test Method

Figure 7:
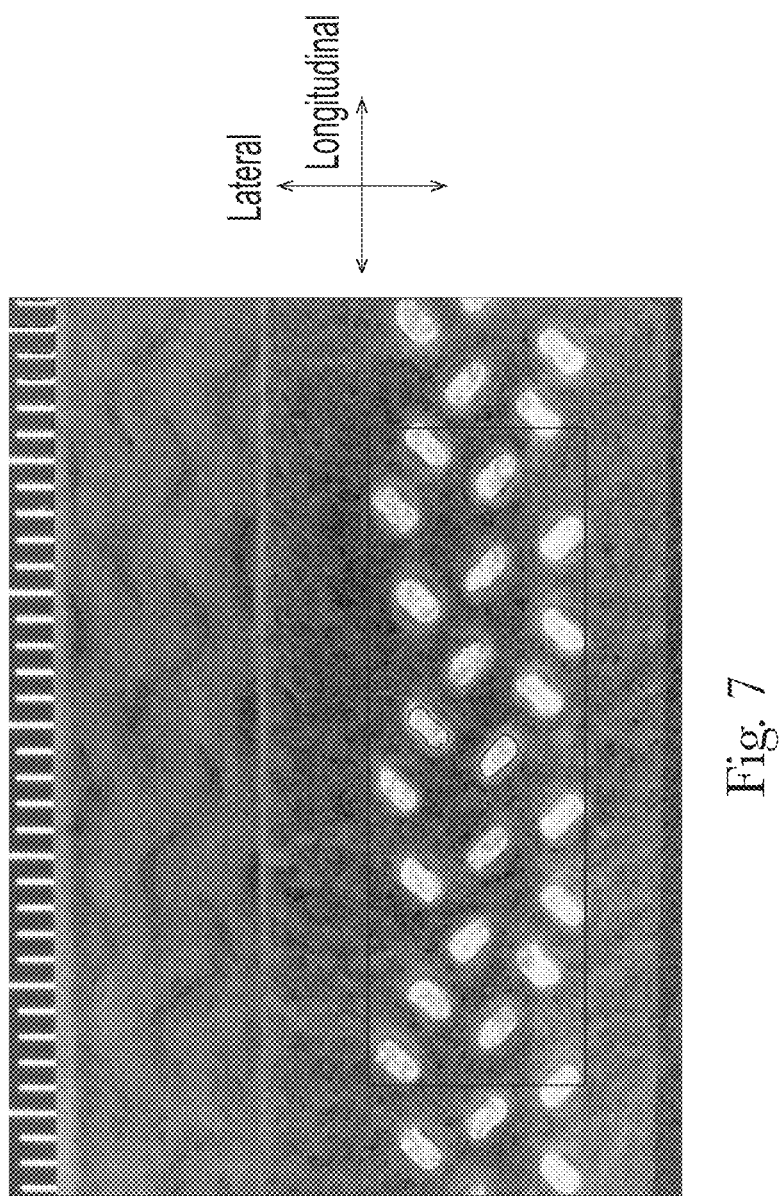
FIG. 7 is a microphotograph of an exemplary composite in accordance with a nonlimiting embodiment of the present invention.

The Bond Dimension Test is used to measure bond density of a bonding region in a composite. The Bond Dimension Test is performed on reflected light microscopy images generated using a stereo light microscope (such as Zeiss V20 Stereoscope) and attached camera (such as the Carl Zeiss AxioCam MRc5). Measurements are performed using Image Pro Plus software (Version 7.0.0.591, Media Cybernetics, USA) calibrated against a ruler that was placed within the image when it was acquired. For purposes of this method, a bond is the intentional joining of two or more layers and is the deformed area caused during the bonding process (e.g., the reduced caliper at the site of bonding). To measure bond density of the bonding region having a uniform pattern, identify the plurality of bonds of interest and outline the resulting periphery in a rectilinear specimen of at least 2 cm$^2$ area and collect by cutting along the periphery. Care should be taken to avoid collecting specimen from an adjacent region if it is different (e.g., unpatterned, unbonded). The specimen is collected in a substantially rectangular shape having at least a 2 cm$^2$ area, such that two lines parallel to the bonding region's longitudinal direction are selected to coincide with the lateral periphery of the bonding region (as shown in FIG. 7), and two shorter dimension lateral lines are selected in such a way to complete the specimen's rectangular area of 2 cm$^2$. If a sufficiently large sample is not available, a smaller sample with a minimum of one repeat bond pattern cell can be used, and the measured bond area values are normalized to the 2 cm$^2$ specimen area. If the pattern is too large for stereoscope imaging, a SLR Camera (such as Pentax R20D) or scanner (such as Epson Perfection V750 Pro Flatbed Scanner) with a black background behind sample should be used to collect the image. If the bonding region includes one or more larger discrete bonds, one of the larger discrete bonds should be centered between the two lateral lines that create the 2 cm$^2$ specimen.

A ruler is placed in each image parallel to the bonds patterns longitudinal direction when the image was acquired. Minimum Bond Spacing is measured with the line tool in Image Pro Plus software. Discrete Bond Area is measured with the irregular area tool in Image Pro Plus software by selecting only the darker area of the bond and excluding the adjacent periphery that appears as a lighter grey scale, as shown with the white ellipse line within the bond sites in FIG. 7, which depicts examples of selecting the Discrete Bond Area within the drawn 2 cm$^2$ rectangle specimen. All specified measurements are measured to accuracy of 0.01 mm or 0.01 mm$^2$ accuracy.

All Discrete Bond Areas within the specimen are added to calculate Aggregate Bond Area for the specimen and then the Aggregate Bond Area is divided by the area of the specimen to determine bond density, and can be expressed with the following formula:

$$\text{Bond Density \%} = \left(\frac{\text{Aggregate Bond Area, mm}^2}{\text{Specimen Area, mm}^2}\right) \times 100$$

If only a portion of a discrete bond falls within the 2 cm$^2$, only the area of that portion falling within the 2 cm$^2$ is used in calculating the Aggregate Bond Area. However, only complete discrete bond sites within the 2 cm$^2$ are used in determining the Largest Discrete Bond, Smallest Discrete Bond, and Max Aspect Ratio of Discrete Bond. The Minimum Discrete Bond Area Ratio and Maximum Discrete Bond Area Ratio, Discrete Bond Size Ratio, and Max Aspect Ratio of Discrete Bond are calculated using the following formulas:

$$\text{Minimum Discrete Bond Area Ratio} = \frac{\text{Aggregate Bond Area, mm}^2}{\text{Area of smallest complete discrete bond in specimen, mm}^2}$$

$$\text{Maximum Discrete Bond Area Ratio} = \frac{\text{Aggregate Bond Area, mm}^2}{\text{Area of largest complete discrete bond in specimen, mm}^2}$$

$$\text{Discrete Bond Size Ratio} = \frac{\text{Area of largest complete discrete bond in specimen, mm}^2}{\text{Area of smallest complete discrete bond in specimen, mm}^2}$$

$$\text{Aspect Ratio of Discrete Bond} = \frac{\text{Longest dimension of complete discrete bond in specimen, mm}}{\text{Shortest dimension of the same complete discrete bond in specimen, mm}}$$

The Max Aspect Ratio is the greatest aspect ratio of the bonds within the specimen.

Larger discrete bonds and smaller discrete bonds can be differentiated by the major dimension of the respective bonds, the major dimension being the greatest length in any direction within the bond. If a single discrete bond has a length of 3.5 mm or greater in any direction, the bond is defined as a larger discrete bond. If the greatest length of a discrete bond in any direction is less than 3.5 mm, the bond is defined as a smaller discrete bond. The Aggregate Area of Smaller Bonds is the sum of the individual Discrete Bond Areas of the smaller discrete bonds within the 2 cm$^2$ specimen. The Aggregate Area of Larger Bonds is the sum of the individual Discrete Bond Areas of the larger bonds within the 2 cm$^2$ specimen. If only a portion of a larger or smaller discrete bond falls within the 2 cm$^2$ specimen, only the area of that portion falling within the 2 cm$^2$ is used in calculating the Aggregate Area of Larger Bonds or Aggregate Area of Smaller Bonds respectively.

The Ratio of Larger to Smaller Bonds is calculated using the following formula:

$$\text{Ratio of Larger to Smaller Bonds} = \frac{\text{Aggregate Area of Larger Bonds in the specimen, mm}^2}{\text{Aggregate Area of Smaller Bonds in the specimen, mm}^2}$$

Hysteresis Test Method

The Hysteresis Test can be used to various specified strain values. The Hysteresis Test utilizes a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The specimens are conditioned for 24 hours prior to testing.

The specimen is cut with a dimension of 10 mm in the intended stretch direction of the component X 25.4 mm in the direction perpendicular to the intended stretch direction of the component. A specimen is collected from either an inelastic region or from an elastic region.

Test Protocol

1. Select the appropriate grips and load cell. The grips must have flat surfaces and must be wide enough to grasp the specimen along its full width. Also, the grips should provide adequate force and suitable surface to ensure that the specimen does not slip during testing. The load cell is selected so that the tensile response from the specimen tested is between 25% and 75% of the capacity of the load cell used.

2. Calibrate the tester according to the manufacturer's instructions.

3. Set the distance between the grips (gauge length) at 7 mm.

4. Place the specimen in the flat surfaces of the grips such that the uniform width lies along a direction perpendicular to the gauge length direction. Secure the specimen in the upper grip, let the specimen hang slack, then close the lower grip. Set the slack preload at 5 gram/force. This means that the data collection starts when the slack is removed (at a constant crosshead speed of 13 mm/min) with a force of 5 gram force. Strain is calculated based on the adjusted gauge length ($l_{ini}$), which is the length of the specimen in between the grips of the tensile tester at a force of 5 gram force. This adjusted gauge length is taken as the initial specimen length, and it corresponds to a strain of 0%. Percent strain at any point in the test is defined as the change in length relative to the adjusted gauge length, divided by the adjusted gauge length, multiplied by 100.

5(a) First cycle loading: Pull the specimen to the 100% strain at a constant cross head speed of 70 mm/min. Report the stretched specimen length between the grips as $l_{max}$.

5(b) First cycle unloading: Hold the specimen at the 100% strain for 30 seconds and then return the crosshead to its starting position (0% strain or initial sample length, $l_{ini}$) at a constant cross head speed of 70 mm/min. Hold the specimen in the unstrained state for 1 minute.

5(c) Second cycle loading: Pull the specimen to the 100% strain at a constant cross head speed of 70 mm/min.

5(d) Second cycle unload: Next, hold the specimen at the 100% strain for 30 seconds and then return the crosshead to its starting position (i.e. 0% strain) at a constant cross head speed of 70 mm/min.

A computer data system records the force exerted on the sample during the test as a function of applied strain. From the resulting data generated, the following quantities are reported.

i. Length of specimen between the grips at a slack preload of 5 gram-force ($l_{ini}$) to the nearest 0.001 mm.

ii. Length of specimen between the grips on first cycle at the 100% strain ($l_{max}$) to the nearest 0.001 mm.

iii. Length of specimen between the grips at a second cycle load force of 7 gram-force ($l_{ext}$) to the nearest 0.001 mm.

iv. % Set, which is defined as $(l_{ext}-l_{ini})/(l_{max}-l_{ini})*100\%$ to the nearest 0.01%. The testing is repeated for six separate samples and the average and standard deviation reported.

Composite Tensile Test Method

Figure 9:
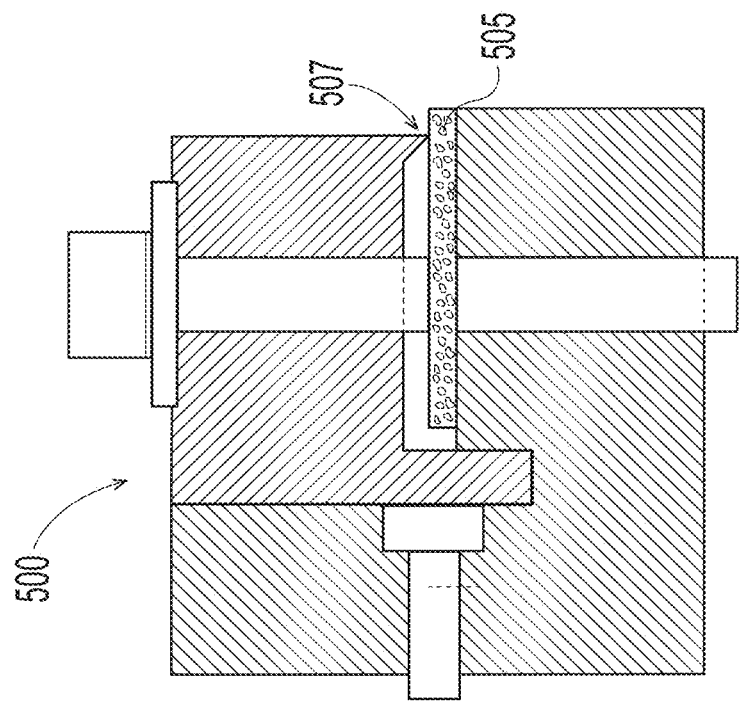
FIG. 9 is a schematic, side elevation view of a grip suitable for use in the Composite Tensile Test Method herein.
Figure 8:
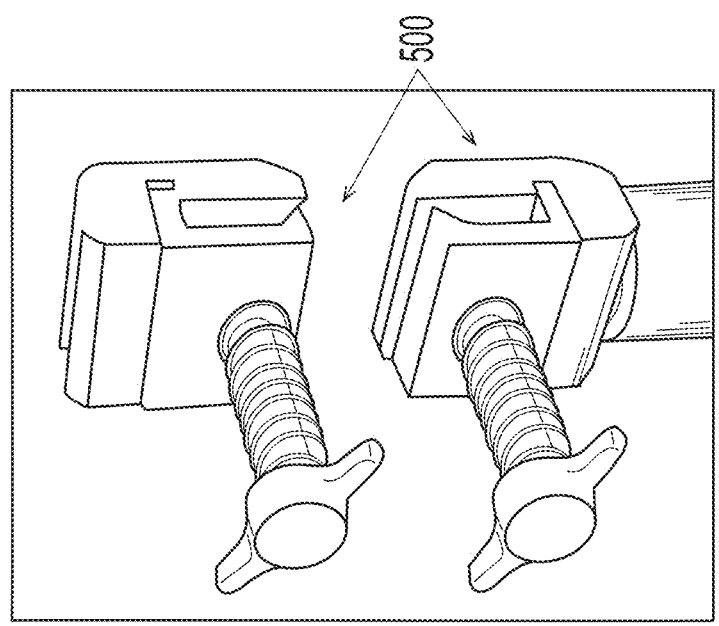
FIG. 8 is a schematic, perspective view of grips suitable for use in the Composite Tensile Test Method herein.

The Composite Tensile Test is used to measure the strength of a specimen at a relatively high strain rate that represents product application. The method uses a suitable tensile tester such as an MTS 810, available from MTS Systems Corp., Eden Prairie Minn., or equivalent, equipped with a servo-hydraulic actuator capable of speeds exceeding 5 m/s after 28 mm of travel, and approaching 6 m/s after 40 mm of travel. The tensile tester is located in a temperature-controlled room at 22° C.±2° C. and 50±10% relative humidity. The tensile tester is fitted with a 50 lb. force transducer (e.g., available from Kistler North America, Amherst, N.Y. as product code 9712 B50 (50 lb)), and a signal conditioner with a dual mode amplifier (e.g., available from Kistler North America as product code 5010). Grips shown in the FIGS. 8 and 9 should be used to secure the specimens during tensile testing. (FIG. 9 is a side view of one of the grips in FIG. 8 with a material 505 to prevent slippage.)

(a) Grips

The line grips are selected to provide a well-defined gauge and avoid undue slippage. The specimen is positioned such that it has minimal slack and the specimen is centered between the grips. The apexes 507 of the grips are ground to give good gauge definition while avoiding damage or cutting of the specimen. The apexes are ground to provide a radius in the range of 0.5-1.0 mm. A portion of one or both grips may be configured to include a material 505 that reduces the tendency of a specimen to slip, (e.g., a piece of urethane or neoprene rubber having a Shore A hardness of between 50 and 70) as shown in FIG. 9. 26 mm wide top and bottom grips are used to clamp the specimen.

(b) Composite Tensile Test of Specimen from Absorbent Article

Figure 10:
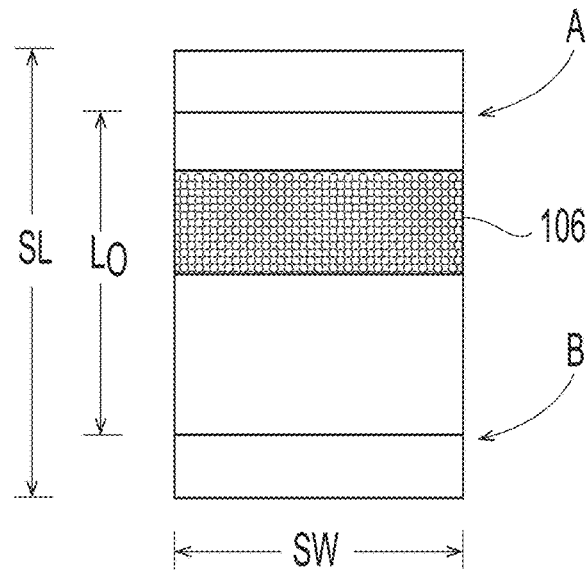
FIG. 10 is a schematic, plan view of a specimen for use in the Composite Tensile Test Method herein.
Figure 11:
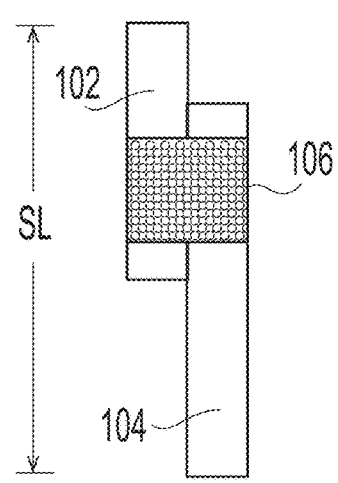
FIG. 11 is a schematic, side elevation view of a specimen for use in the Composite Tensile Test Method herein.

A minimum of four specimens are collected and cut from the same portion of identical absorbent article products, and care should be taken to prevent damage of the specimen during the separation process. The longitudinal direction (i.e., the maximum linear dimension) of the bonding region is determined. A specimen measuring 32 mm in the lateral direction (i.e., perpendicular to the longitudinal direction of the bond) (SL) by 25 mm in the longitudinal direction (SW) of a given composite web is delicately cut from the article with the bonding region positioned in order to have one longitudinal edge of the bond centered in the lengthwise middle of the specimen, as shown in FIG. 10, which schematically depicts a front view of the specimen and the grip line A and B. The specimen is tested as follows: The gauge length, $L_0$, (i.e. grip to grip separation) of the vertical, lengthwise distance from the first grip location, to the second grip location is 25 mm, and is measured to 0.1 mm accuracy using a ruler. The specimen is tested at a test speed that provides a cross-head displacement speed of approximately 0.5 m/s. Before testing, 5 mm of slack is put between the grips. The specimen is placed between the grips 500 such that the longitudinal dimension of the bonding region of the specimen will be parallel to the grip apexes, where the first grip is holding the first substrate at Grip Line A and the second grip is holding the second substrate at Grip Line B, thereby testing the Composite Tensile Strength of the connection between the substrate during the testing, as shown for example in FIG. 11. If the second substrate is long enough to extend to the Grip Line A position or the first substrate is long enough to extend to the Grip Line B position, this excess material should be delicately folded to prevent it from entering the incorrect the respective grip.

Each tensile curve force is normalized for the specimen lateral dimension using the following formula:

$$\text{Force}\frac{N}{\text{cm}} = \left(\frac{\text{Force, Newtons}}{\text{specimen width, cm}}\right)$$

The strain of each specimen is reported on the x axis in % Strain while the force of each specimen is reported on the y axis in Force (N/cm). The % strain is calculated from the extended length between grip lines, L, and initial gauge length, $L_0$, using the following formula:

$$\% \text{ Strain} = \frac{(L - L_0)}{L_0} \times 100$$

Each specimen is pulled until it ruptures (i.e. the post peak force response reaches a value less than 10% of the peak force). During testing, one of the grips is kept stationary and the opposing grip is moved. The force and actuator displacement data generated during the test are recorded using a MOOG SmarTEST ONE STO03014-205 standalone controller, with the data acquisition frequency set at 10 kHz. Peak Force value is recorded as the Composite Tensile Strength of the specimen tested. Peak is defined as the maximum force value followed by substantial drop in force, as opposed to Break which is defined as the point where the material fractures or ruptures, and force drops rapidly to zero value. % Strain at Peak is defined as the % Strain at the maximum force.

The Average % Strain at Peak, Average Composite Tensile Strength (N/cm) and standard deviation of at least 4 specimens are recorded. If, standard deviation recorded is higher than 15%, a new set of four specimens is tested. Averages are the arithmetic averages.

(a) Tensile Test of a Substrate

A minimum of four specimens are collected and cut from the same portion of identical absorbent article products, and care should be taken to prevent damage of the specimen during the separation process. A specimen having the same dimensions and directional orientations as the composite specimens is delicately cut from the article adjacent to the bond pattern, avoiding the bonding region such that when tested failure will occur in the substrate. The specimens are tested in the same manner as the composite specimens, except each grip holds the same substrate. Peak Force, as defined before, is recorded as Peak Force Tensile Strength or Tensile Strength at Peak Force of the substrate specimen. The arithmetic average of Specimen Substrate Tensile Strength at Peak Force (N/cm) and standard deviation of at least 4 specimens is recorded, and reported as the Average Tensile Strength at Peak Force or Average Peak Force Tensile Strength. If, standard deviation recorded is higher than 15%, a new set of four specimens is tested.

Longitudinal Peel Strength Test Method

A suitable tensile tester interfaced with a computer such as MTS model Alliance RT/1 with TestWorks 4® software or equivalent is used. The tensile tester is located in a temperature-controlled room at 22° C.±2° C. and 50±10% relative humidity. The instrument is calibrated according to the manufacturer's instructions. The data acquisition rate is set to at least 50 Hertz. The grips used for the test are wider than the sample. Grips having 50.8 mm width may be used. The grips are air actuated grips designed to concentrate the entire gripping force along a single line perpendicular to the direction of testing stress having one flat surface and an opposing face from which protrudes a half round (radius=6 mm, e.g. part number: 56-163-827 from MTS Systems Corp.) or equivalent grips, to minimize slippage of the sample. The load cell is selected so that the forces measured are between 10% and 90% of the capacity of the load cell used. The initial distance between the lines of gripping force (gauge length) is set at 25.4 mm. The load reading on the instrument is zeroed to account for the mass of the fixture and grips.

Figure 12:
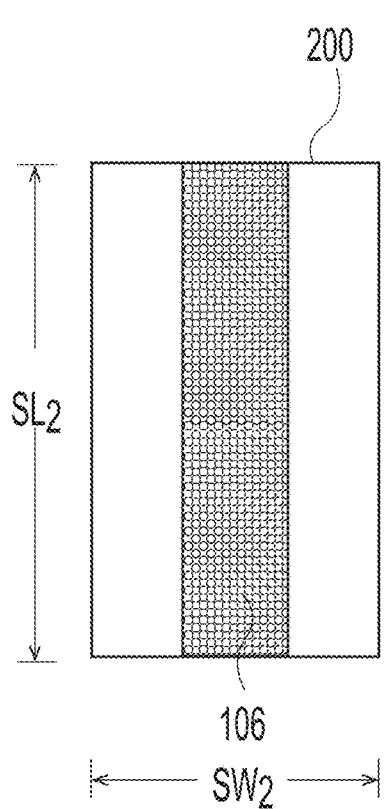
FIG. 12 is a schematic, plan view of a specimen for use in the Longitudinal Peel Test Method herein.
Figure 13:
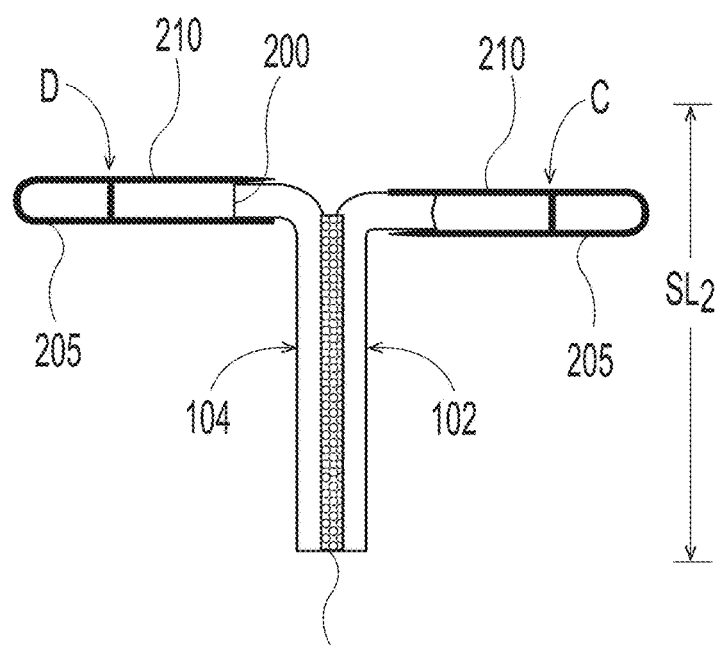
FIG. 13 is a schematic, side elevation view of a specimen for use in the Longitudinal Peel Test Method herein.

A minimum of four specimens are collected and cut from the same portion of identical absorbent article products, and care should be taken to prevent damage of the specimen during the separation process. The longitudinal direction (i.e., the maximum linear dimension) of the bonding region is determined. A specimen measuring 110 mm in the longitudinal direction of the bonding region, SL2, by 25 mm in the transverse direction, $SW_2$, of a given composite web is delicately cut from the absorbent article with the bonding region positioned in the widthwise middle of the specimen, as shown in FIG. 12. Starting at one of the transverse ends 200 of the specimen, the specimen peel is initiated by delicately separating the first substrate 102 from the second substrate 104 at the bonded junction by using tweezers or delicate fingers, until approximately 5 mm the first substrate has been separated from second substrate. A 30 to 40 mm long section of 25 mm wide tape 210, such as 3M SCOTCH® 234, is then used to attach to the first substrate, creating a tape leader 205 to increase the length of the loose material, as shown in FIG. 13. A standard office stapler is used to staple the tape leader onto the first substrate to ensure that the Tape Leader does not separate during the peel test. Additionally, a tape leader and staple is also added to the second substrate by following the same outlined procedure.

The specimen is mounted into the grips in a manner such that there is no slack and the load measured is between 0.00 N and 0.02 N. The specimen is mounted in the center of the grips, such that the specimen peeling direction is parallel to the applied tensile stress. The specimen is placed between the grips such that the longitudinal dimension of the bonding region will be perpendicular to the grip apexes, where the first grip is holding tape leader with the first substrate at Grip Line C and the second grip is holding tape leader with the second substrate at Grip Line D, thereby peeling the first substrate from the second substrate in a 180° peeling direction. A skilled artisan should recognize that bonded specimens of other dimensions may be used in the Longitudinal Peel Method; however, the effective bonded area should remain centered in the specimen. The peel test is initiated and the specimen is extended at 127 mm/min, with a data acquisition rate of at least 50 Hertz, until the specimens separate completely. The peel displacement of each specimen is reported on the x axis in millimeters of crosshead travel, while the force of each specimen is reported on the y axis in Force (N, Newtons). The Peel Strength Force (N) is averaged from 10 mm to approximately 100 mm of peel displacement, and this is reported as the Specimen Longitudinal Peel Strength. The arithmetic average of the Specimen Longitudinal Peel Strength in N and standard deviation of at least 4 specimens is recorded and reported as the Average Longitudinal Peel Strength (N). If, standard deviation recorded is higher than 20%, a new set of four specimens is tested.

Lateral Peel Strength Test Method

A suitable tensile tester interfaced with a computer such as MTS model Alliance RT/1 with TestWorks 4® software or equivalent is used. The tensile tester is located in a temperature-controlled room at 22° C.±2° C. and 50±10% relative humidity. The instrument is calibrated according to the manufacturer's instructions. The data acquisition rate is set to at least 50 Hertz. Grips as described in the Composite Tensile Test Method herein and shown in the FIGS. 8 and 9 should be used to secure the specimens during tensile testing, except 154 mm wide top and bottom grips are used to clamp the specimen. The initial distance between the lines of gripping force (gauge length) is set at 10 mm. The load reading on the instrument is zeroed to account for the mass of the fixture and grips.

Figure 14:
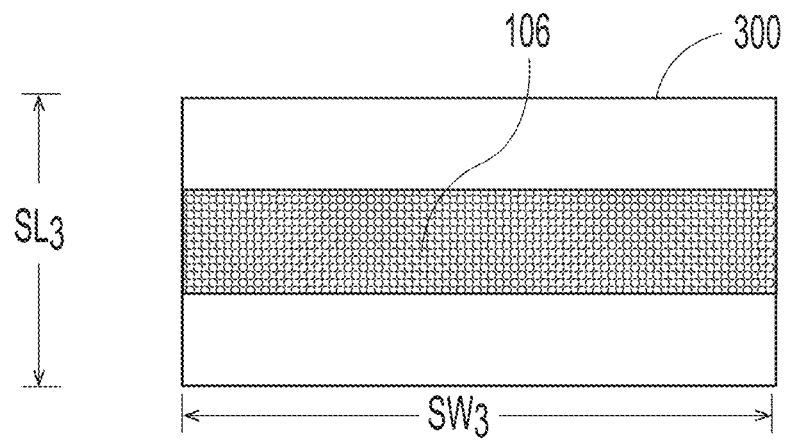
FIG. 14 is a schematic, plan view of a specimen for use in the Lateral Peel Test Method herein.

A minimum of four specimens are collected and cut from the same portion of identical absorbent article products, and care should be taken to prevent damage of the specimen during the separation process. The longitudinal direction (i.e., the maximum linear dimension) of the bonding region is determined. A specimen measuring 25 mm in lateral direction of the bonding region, $SL_3$, by 107 mm in the longitudinal dimension of the bonding region, $SW_3$, of a given composite web is delicately cut from the absorbent article with the bonding region positioned in the lengthwise middle of the specimen, as shown in FIG. 14. Starting at a lengthwise end 300 of the specimen, the specimen is delicately inspected to ensure that there is sufficient unbonded loose edges of the first or second substrate to fit securely into the grips, i.e. collectively the first and second substrate have greater than 10 mm of unbonded loose edge. A skilled artisan should recognize that if there is not sufficient unbonded loose edges of the first or second substrate to fit securely into the grips, the initial distance between the lines of gripping force (gauge length) can be adjusted to less than 10 mm. Alternatively, a tape leader 205 can be used by following the procedure outlined in the Longitudinal Peel Strength Test Method, with care to delicately handle the specimens in order to prevent any premature separation of first and second substrates.

Figure 15:
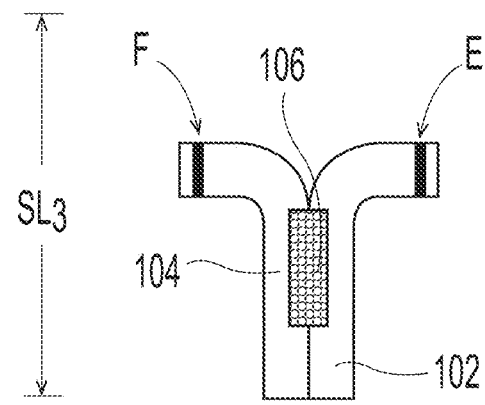
FIG. 15 is a schematic, side elevation view of a specimen for use in the Lateral Peel Test Method herein.

The specimen is mounted into the grips in a manner such that there is no slack and the load measured is between 0.00 N and 0.02 N. The specimen is mounted in the center of the grips, such that the specimen peeling direction is parallel to the applied tensile stress. The specimen is placed between the grips such that the longitudinal dimension of the bonding region will be parallel to the grip apexes, where the first grip holding the first substrate at Grip Line E and the second grip is holding the seconds substrate at Grip Line F as shown in FIG. 15, thereby peeling the first substrate from the second substrate in a 180° peeling direction. A skilled artisan should recognize that bonded specimens of other dimensions may be used in the Lateral Peel Method; however, the effective bonded area should remain centered in the specimen and the Lateral Peel Force should be normalized by the specimen width, $SW_3$, using the following formula:

$$\text{Force} \frac{N}{cm} = \left( \frac{\text{Force, Newtons}}{\text{specimen width, cm}} \right)$$

The peel test is initiated and the specimen is extended at 127 mm/min, with a data acquisition rate of at least 50 Hertz, until the specimens separate completely. The peel displacement of each specimen is reported on the x axis in millimeters of crosshead travel, while the force of each specimen is reported on the y axis in Force (N/cm). The Lateral Peak Peel Strength in N/cm is recorded, where Peak is defined as the maximum force value followed by substantial drop in force. The specimen's Lateral Peel Strength is recorded by averaging the Peel Force in N/cm over the entire peeling displacement. The arithmetic average of the Lateral Peak Peel Strength (N/cm) and standard deviation of at least 4 specimens is recorded and reported as the Average Lateral Peak Peel Strength. The arithmetic average of Specimen Lateral Peel Strength (N/cm) and standard deviation of at least 4 specimens is also recorded and reported as the Average Lateral Peel Strength (N/cm). If, standard deviation recorded is higher than 20%, a new set of four specimens is tested.

Topsheet AGM Residue Method

The Topsheet AGM Residue (TAGMR) Method is used to assess the presence of AGM particles on the skin-facing side of the topsheet of an absorbent article. In this method, like samples of absorbent articles are stretched flat with skin-facing side facing up and are misted with aqueous copper sulfate solution. AGM particles are colored blue by the copper sulfate, and the prevalence of AGM particles is visually assessed. All testing is conducted in a conditioned room at a temperature of 23° C.±2.0° C. and a relative humidity of 45%±10% on samples that have been conditioned for a minimum of 12 hours to these same conditions prior to the test.

Ten nominally equivalent samples of absorbent articles are selected at random. For each sample article, the elastic leg cuffs are removed, and the sample is held flat on a board outfitted with adhesive or hook material. With a handheld pump sprayer, 15±5 mL of a 0.5% w/w aqueous solution of copper sulfate is sprayed approximately uniformly across the topsheet of the article. Within 1 minute of delivery of this solution, the topsheet is visually assessed, and the number of distinct AGM particles observed on the topsheet is recorded.

The arithmetic mean of number of particles observed across the ten samples is calculated and reported to the nearest integer as the Average Number of Particles Per Pad. The number of samples for which no particles were observed is divided by 10 (the total number of samples) and reported as a percentage as the Percentage of Pads with No Residue Particles.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 16). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a topsheet, backsheet and absorbent core disposed between the topsheet and backsheet and a composite; the composite comprising a first substrate and a second substrate joined in a bonding region, wherein:

the first substrate comprises a first Average Peak Force Tensile Strength and the second substrate has a second Average Peak Force Tensile Strength, wherein the first Average Peak Force Tensile Strength is greater than the second Average Peak Force Tensile Strength; and the bonding region comprises:

a plurality of discrete bonds disposed in a pattern, wherein the pattern has a repeat unit comprising from about 5 bonds to about 15 bonds;

a Bond Density of about 10% to about 22%; and an Average Composite Tensile Strength that is within about 15% of the second Average Peak Force Tensile Strength.

2. The absorbent article of claim 1 wherein the plurality of discrete bonds comprises a plurality of mechanical bonds.

3. The absorbent article of claim 2 wherein the bonding region further comprises adhesive bonding.

4. The absorbent article of claim 1 wherein the bonding region consists essentially of discrete bonds oriented off-axis.

5. The absorbent article of claim 1 wherein the bonding region comprises a Discrete Bond Size Ratio of not more than about 7.

6. The absorbent article of claim 1 wherein a majority of the discrete bonds comprise a major dimension of less than 3.5 mm.

7. The absorbent article of claim 1 wherein the bonding region comprises a Minimum Bond Spacing of about 0.9 mm or greater.

8. The absorbent article of claim 1 wherein the bonding region comprises a longitudinally and/or laterally interlocking bond pattern.

9. The absorbent article of claim 1 wherein the bond region comprises a Minimum Discrete Bond Area Ratio of from about 20 to about 105 and/or a Maximum Discrete Bond Area Ratio of from about 8 to about 25.

10. The absorbent article of claim 1 wherein the plurality of discrete bonds comprises one or more bond having a major dimension of 3.5 mm or greater and the bonding region comprises a Ratio of Larger to Smaller Bonds of 2 or less.

* * * * *